(12) United States Patent
Johnsson et al.

(10) Patent No.: US 9,952,208 B2
(45) Date of Patent: Apr. 24, 2018

(54) MEANS AND METHODS FOR BIOLUMINESCENCE RESONANCE ENERGY TRANSFER (BRET) ANALYSIS IN A BIOLOGICAL SAMPLE

(71) Applicant: Ecole Polytechnique Fédérale de Lausanne, Lausanne (CH)

(72) Inventors: Kai Peter Johnsson, Neuchatel (CH); Alberto Schena, Renens (CH); Rudolf Griss, Morges (CH)

(73) Assignee: Ecole Polytechnique Fédérale de Lausanne, Lausanne (CH)

( * ) Notice: Subject to any disclaimer, the term of this patent is extended or adjusted under 35 U.S.C. 154(b) by 108 days.

(21) Appl. No.: 14/905,654

(22) PCT Filed: Jul. 18, 2013

(86) PCT No.: PCT/EP2013/065223
§ 371 (c)(1),
(2) Date: Jan. 15, 2016

(87) PCT Pub. No.: WO2015/007317
PCT Pub. Date: Jan. 22, 2015

(65) Prior Publication Data
US 2016/0146794 A1    May 26, 2016

(51) Int. Cl.
*G01N 33/542* (2006.01)
*C12Q 1/66* (2006.01)
*G01N 21/76* (2006.01)
*G01N 21/75* (2006.01)

(52) U.S. Cl.
CPC ............. *G01N 33/542* (2013.01); *C12Q 1/66* (2013.01); *G01N 21/763* (2013.01); *G01N 2021/757* (2013.01); *G01N 2333/90241* (2013.01)

(58) Field of Classification Search
None
See application file for complete search history.

(56) References Cited

U.S. PATENT DOCUMENTS

| 5,196,524 | A | 3/1993 | Gustafson et al. |
| 5,219,737 | A | 6/1993 | Kajiyama et al. |
| 5,229,285 | A | 7/1993 | Kajiyama et al. |
| 5,670,356 | A | 9/1997 | Sherf et al. |

(Continued)

FOREIGN PATENT DOCUMENTS

| WO | WO-2012061530 A2 | 5/2012 |
| WO | WO-2015007317 A1 | 1/2015 |

OTHER PUBLICATIONS

"International Application Serial No. PCT/EP2013/065223, International Written Opinion dated Mar. 26, 2014", 10 pgs, 2014.

(Continued)

*Primary Examiner* — Changhwa J Cheu
(74) *Attorney, Agent, or Firm* — Schwegman Lundberg & Woessner, P.A.

(57) ABSTRACT

The invention relates to the field of in vitro detection methods using luminescence. Provided is a sensor molecule for detecting an analyte of interest in a sample using bioluminescence resonance energy transfer (BRET), the sensor molecule comprising a proteinaceous moiety tethered to a synthetic regulatory molecule. Also provided is an analytical device comprising a sensor and methods using the sensor molecule.

19 Claims, 14 Drawing Sheets

(56) References Cited

Figure 1C:
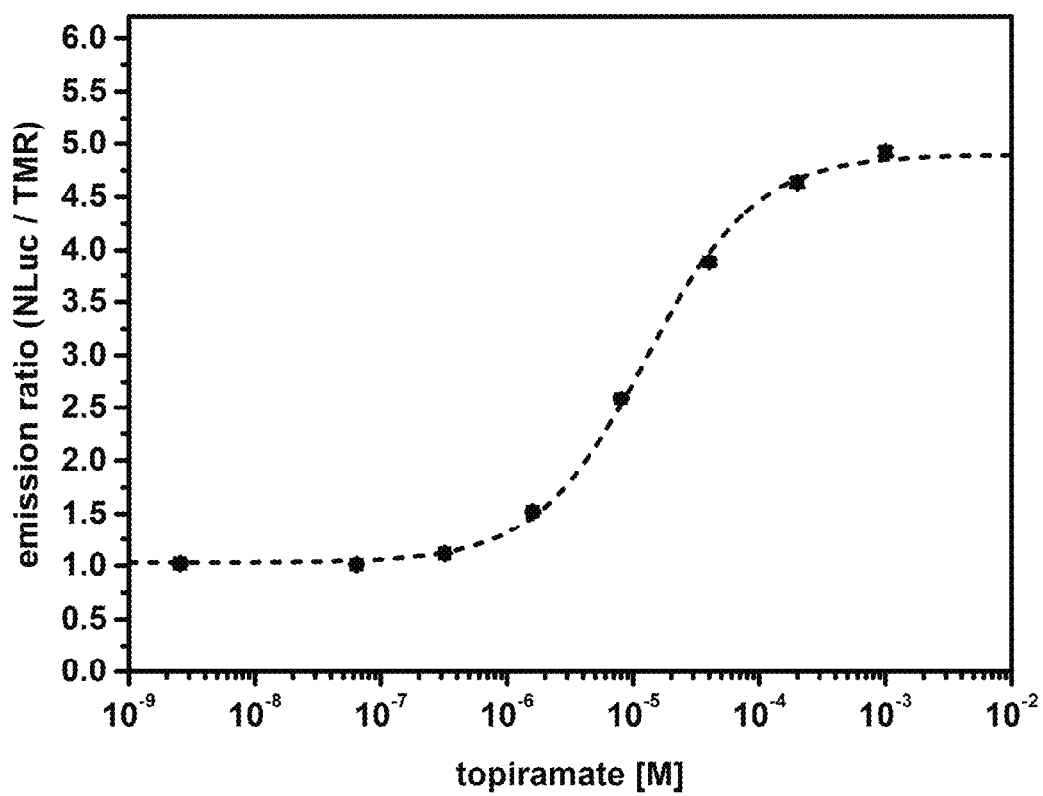

U.S. PATENT DOCUMENTS 5,843,746 A   12/1998   Tatsumi et al.

OTHER PUBLICATIONS

Beckett, Dorothy, et al., "A minimal peptide substrate in biotin holoenzyme synthetase-catalyzed biotinylation", Protein Science, (Jan. 1999), 921-929.

Brun, Matthias A., et al., "A Semisynthetic Fluorescent Sensor Protein for Glutamate", Journal of the American Chemical Society, (2012), 7676-7678.

Brun, Matthias A., et al., "Semisynthesis of Fluorescent Metabolite Sensors on Cell Surfaces", J. Am Chem. Soc., 133, (2011), 16235-16242.

Brun, Matthias A., et al., "Semisynthetic Fluorescent Sensor Proteins Based on Self-Labeling Protein Tags", J, Am. Chem. Soc. 2009, 131, (2009), 5873-5884.

Fleishman, Sarel J., et al., "Computational Design of Proteins Targeting the Conserved Stem Region of Influenza Hernagglutinin", Sciencemag.org vol. 332, (May 13, 2011), 816-821.

George, Nathalie, et al., "Specific Labeling of Cell Surface Proteins with Chemically Diverse Compounds", J. Am. Chem. Sac, 126, (Jul. 3, 2004), 8896-8897.

Hall, Mary P., et al., "Engineered Luciferase Reporter from a Deep Sea Shrimp Utilizing a Novel lmidazopyrazinone Substrate", ACS Publications, (2012), 1848-1857.

Iwakura, Masahiro, et al., "Effects of the length of a glycine linker connecting the N- and C-termini of a circularly permuted dihydrofolate reductase", Protein Engineering vol. 11 No. 8, (1998), 707-713.

Jonkheijm, Pascal, et al., "Chemical Strategies for Generating Protein Biochips", Angew. Chem. Int. Ed. 2008, 47, (2008), 9618-9647.

Kvach, Maksim V., et al., "Practical Synthesis of Isornerically Pure 5- and 6-Carboxytetramethylrhodarnines, Useful Dyes for DNA Probes", Bioconjugate Chem. 2009, 20, (2009), 1673-1682.

Liu, Daniel S., et al., "Diels-Alder Cycloaddition for Fluorophore Targeting to Specific Proteins inside Living Cells", J. Am. Chem. Soc. 2012, 134, (2012), 792-795.

Masharina, Anastasiya, et al., "A Fluorescent Sensor for GABA and Synthetic GABAB Receptor Ligands", J. Am. Chem. Soc. 2012, 134, (2012), 19026-19034.

Matthiesen, Karina, et al., "Cyclic AMP Control Measured in Two Compartments in HEK293 Cells: Phosphodiesterase kM is More Important than Phosphodiesterase Localization", PLoS One vol. 6 Issue 9, (Sep. 2011), 8 pgs.

Muir, Tom W., "Semisynthesis of Proteins by Expressed Protein Ligation", Annu. Rev. Biochem. 2003. 72:, (2003), 249-289.

Mujumgar, Ratnakar B., "Cyanine Dye Labeling Reagents: Sulfoindocyanine Succinimidyl Esters", American Chemical Society, vol. 4, No. 2, (1993), 7 pgs.

Pollock, Nira R., et al., "A Paper-Based Multiplexed Transaminase Test for Low-Cost, Point-of-Care Liver Function Testing", Science Translational Medicine vol. 4 Issue 152, (Sep. 19, 2012), 12 pgs.

Salahpour, Ali, et al., "BRET biosensors to study GPCR biology, pharamcology and signal transduction", Frontiers in Endocrinology vol. 3 Article 105, (Aug. 2012), 9 pgs.

Schann, Stephan, et al., "Technology combination to address GPCR allosteric modulator drugdiscovery pitfalls", Drug Discovery Today: Technologies vol. 10, (Nov. 2013), e261-e267.

Skerra, Arne, "Alternative binding proteins: Anticalins—harnessing the structural plasticity of the lipocalin ligand pocket to engineer novel binding activities", FEBS Journal 275, (2008), 2677-2683.

Tinberg, Christine E., et al., "Computational design of ligand-binding proteins with high affinity and selectivity", Nature vol. 501, (Sep. 12, 2013), 7 pgs.

Volkmann, Gerrit, "Protein C-Terminal Labeling and Biotinylation Using Synthetic Peptide and Split-Intein", PLoS One 4(12): e8381, (Dec. 2009), 12 pgs.

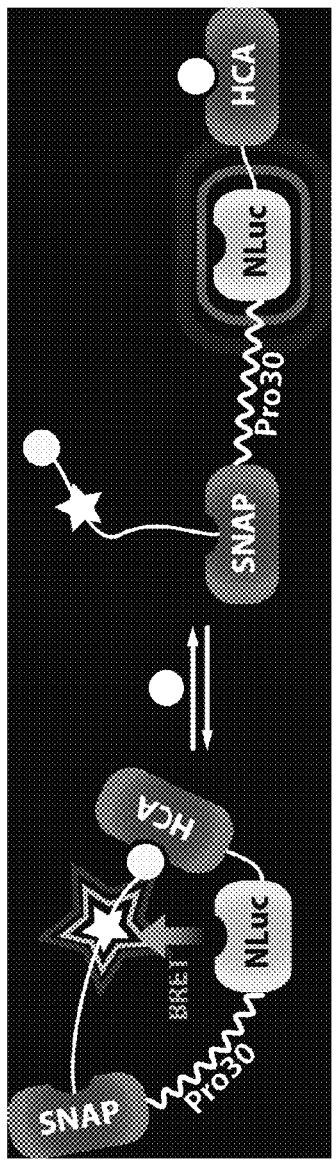
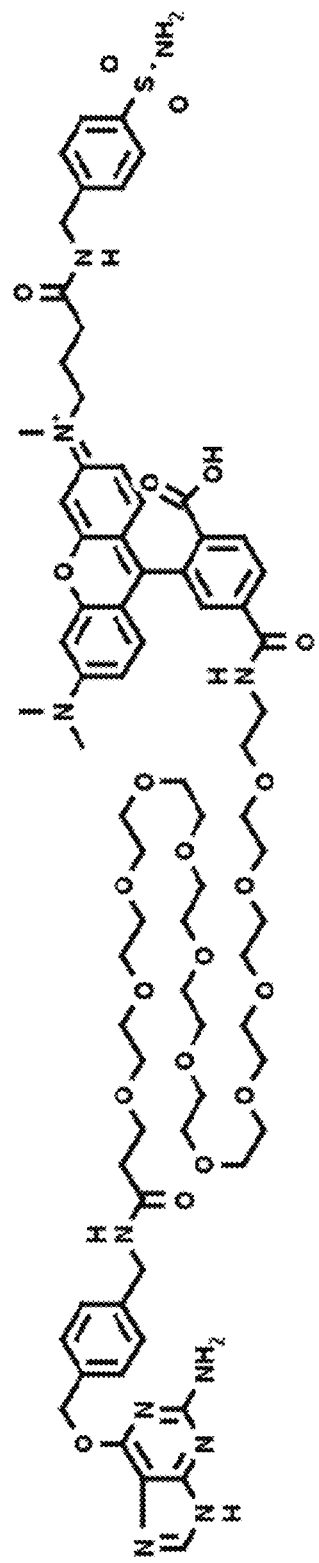
Fig. 1A
Fig. 1B

Figure 2C:
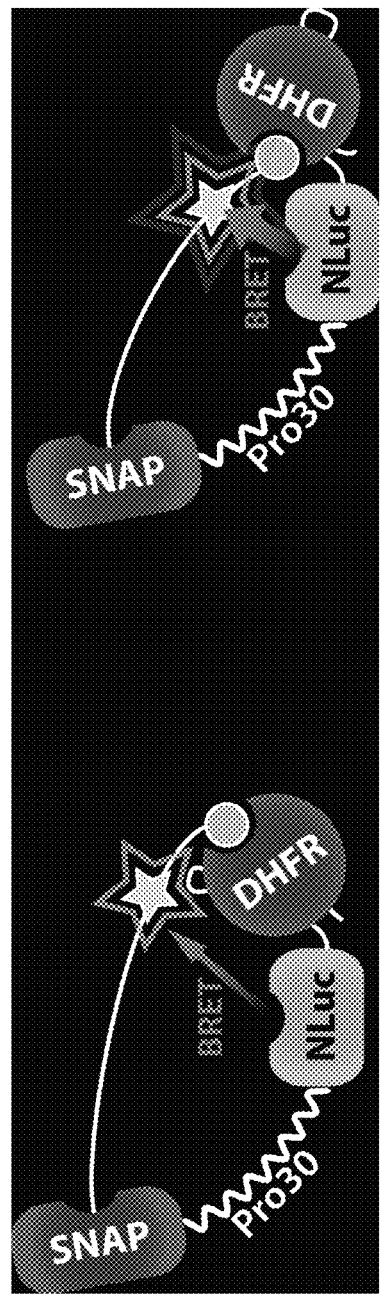

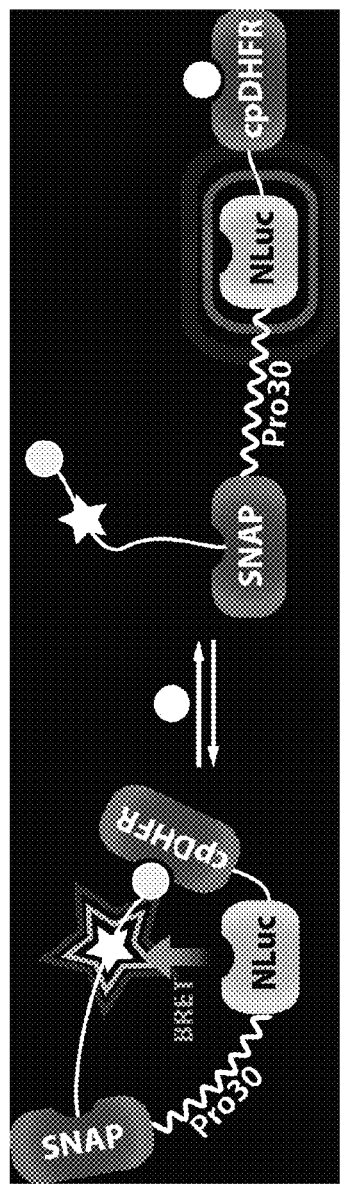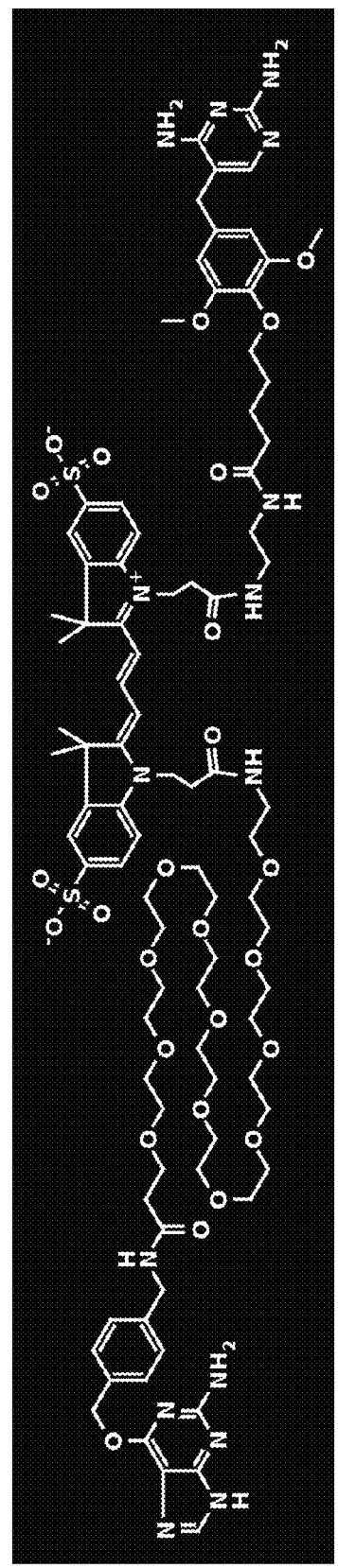
Fig. 2A
Fig. 2B

MEANS AND METHODS FOR BIOLUMINESCENCE RESONANCE ENERGY TRANSFER (BRET) ANALYSIS IN A BIOLOGICAL SAMPLE

PRIORITY APPLICATIONS

This application is a U.S. National Stage Filing under 35 U.S.C. 371 from International Application No. PCT/EP2013/065223, filed on 18 Jul. 2013, and published as WO 2015/007317 on 22 Jan. 2015; which application and publication are incorporated herein by reference in its entirety.

The invention relates to the field of in vitro detection methods using luminescence. Luminescence is a phenomenon in which energy is specifically channeled to a molecule to produce an excited state. Return to a lower energy state is accompanied by release of a photon. Luminescence includes fluorescence, phosphorescence, chemiluminescence, and bioluminescence. Luminescence can be used, among others, in the analysis of free analytes or biological interactions.

In 2009, the inventor introduced an approach for the generation of semisynthetic protein-based biosensors for small molecule analytes. The fluorescent biosensors were named SNap-tag Indicator protein with a Fluorescent Intramolecular Tether (Snifit). See Brun et al. J Am Chem Soc. 2009; 131(16):5873-84 and Brun et al. J Am Chem Soc. 2011; 133(40):16235-42.

Importantly, Snifits are ratiometric sensors comprised of a single molecule, which permits to make sensor readout independent of the actual sensor concentration. The Snifit sensor consists of SNAP-tag, a fluorescent protein and a metabolite-binding protein. SNAP-tag is specifically labeled with a synthetic molecule containing a ligand of the metabolite-binding protein and a fluorophore. In the labeled sensor, the metabolite of interest displaces the intramolecular ligand from the binding protein, thereby shifting the sensor protein from a closed to an open conformation. The readout is a concomitant ratiometric change in the fluorescence intensities of the fluorescent protein and the tethered fluorophore. Thus, the presence or absence of the analyte leads to a conformational switch in the sensor protein so that the position of the two fluorophores relative to each other and therefore also the efficiency of FRET between them (the read-out) changes. By choosing a suitable binding protein and its relative tetherable ligand, virtually any small metabolite can be sensed and several examples have been disclosed. See. Brun et al. J Am Chem Soc. 2012; 134(18):7676-8 and Masharina et al. J Am Chem Soc. 2012; 134(46):19026-34.

However, the currently known Snifit-approach is limited by at least the following shortcomings: (i) the ratio changes are small and no one has yet been able to identify approaches to increase ratio changes by increasing RET efficiency in the closed state; (ii) the direct use of ratiometric RET sensors for quantification of analytes in complex samples that absorb light at the emission wavelengths of the sensor, e.g. serum or other bodily fluids, is prone to artifacts and leads to unreliable assay outcomes.

Numerous attempts to identify a strategy to further improve ratio changes by increased RET-efficiency in the closed sensor using conventional Snifits were unsuccessful (JACS, 2011 (133, 16235-16242). Furthermore, complex samples might contain varying concentrations of fluorescent molecules that would interfere with quantification. Ratiometric readout also will be affected by light absorbance of samples such as serum or other body fluids, thereby making quantifications prone to errors.

Whereas sensors based on luciferases as an internal light source (i.e. BRET) would in theory reduce the fluorescent background problem and potentially increase sensitivity, no ratiometric BRET-based sensors have yet been introduced that are suitably used for the mix-and-measure quantification of analytes in light-absorbing samples.

The fact that no BRET-based, portable, mix-and-measure sensors for precise point-of-care quantification of analytes (e.g. for therapeutic drug monitoring) are currently available despite major developments in (medical) applications of bioluminescence technology is illustrative of the technical difficulties encountered to generate such sensors.

The inventors therefore set out to provide ratiometric, luminescent sensors comprised out of single molecules with improved ratio changes and methods for their use that overcome at least part of the above shortcomings. In particular, they aimed at structural optimization leading to higher signal changes and to make the sensors applicable for direct quantification of analytes such as drugs, metabolites, or proteins in bodily fluids or other complex, light-absorbing samples. Preferably, detection should be compatible with a portable camera or a smartphone.

It was found that these goals could be met by the provision of a specifically designed sensor molecule comprising a proteinaceous moiety comprising a luciferase and a binding partner of the analyte, which moiety is tethered to a fluorophore and an intramolecular ligand competing with the analyte of interest for binding to the binding partner. When, in the absence of analyte, the intramolecular ligand is bound to the binding partner, the fluorophore is in close proximity to the luciferase and strong bioluminescence resonance energy transfer (BRET) occurs when a luciferase substrate is present. In contrast, when the analyte of interest is present in sufficient concentrations to displace the intramolecular ligand, the sensor switches to its open conformation and the increased distance between the luciferase and the synthetic fluorophore leads to a lower BRET-efficiency. See FIGS. 1-4 for a pictorial representation of representative sensors. Surprisingly, it was found that the exchange of a fluorescent protein in Snifits with a luciferase resulted in sensors with significantly (2-fold) increased ratio changes by increasing RET efficiency in the closed state. This unexpected improvement is of great importance for practical applications of the sensors. Furthermore, it was surprisingly found that by absorbing the BRET sensors and the samples to a solid carrier such as paper or by immobilizing the BRET sensors prior to measurement to a solid carrier such as a glass surface, interference from absorbance of the sample at the emission wavelength of the sensor is minimized. This then allows for analysis of complex samples, like serum.

Accordingly, in one embodiment the invention provides a sensor molecule for detecting an analyte of interest in a sample using bioluminescence resonance energy transfer (BRET), the sensor molecule comprising a proteinaceous moiety tethered to a synthetic regulatory molecule, wherein (i) the proteinaceous moiety comprises a luciferase enzyme (Luc) attached to binding protein (BP) capable of binding the analyte of interest;

(ii) the synthetic regulatory molecule comprises a ligand (L) capable of intramolecular binding to BP, and a fluorescent acceptor that can accept energy from the Luc through resonance energy transfer (RET), in the presence of the appropriate Luc substrate, and (iii) wherein the binding of analyte to BP results in a change in the equilibrium between open and closed state of the sensor molecule, thereby resulting in a change in BRET efficiency.

In one embodiment, the binding of analyte and L to BP is mutually exclusive, such that in the absence of analyte L is bound to BP, resulting in a closed conformation of the sensor molecule wherein the fluorescent acceptor is in close spatial proximity to Luc allowing for BRET to occur, and wherein the presence of analyte displaces L from BP resulting in an open conformation of the sensor molecule such that BRET efficiency decreases.

In another embodiment, binding of analyte and L to BP is cooperative, such that in the absence of analyte L is not bound to BP, resulting in a open conformation of the sensor molecule wherein only low BRET efficiency occurs and wherein the binding of analyte to BP induces the cooperative binding of L to BP resulting in an closed conformation of the sensor molecule wherein the fluorescent acceptor is in close spatial proximity to Luc allowing for efficient BRET to occur.

A sensor molecule of the invention is characterized among others by a proteinaceous moiety comprising a luciferase enzyme (Luc) attached to a binding protein (BP) capable of binding the analyte of interest.

As used herein, Luc refers to a luciferase enzyme capable of catalyzing an energy-yielding chemical reaction in which a specific substance, a luciferin, is oxidized. A great diversity of organisms, both prokaryotic and eukaryotic, including species of bacteria, algae, fungi, insects, fish and other marine forms can emit light energy in this manner and each has specific luciferase activities and luciferins which are chemically distinct from those of other organisms. Luciferin/luciferase systems are very diverse in form, chemistry and function. For example, there are luciferase activities which facilitate continuous chemiluminescence, as exhibited by some bacteria and mushrooms, and those which are adapted to facilitate sporadic, or stimuli induced, emissions, as in the case of dinoflagellate algae. As a phenomenon which entails the transformation of chemical energy into light energy, bioluminescence is not restricted to living organisms, nor does it require the presence of living organisms. It is simply a type of chemiluminescent reaction that requires a luciferase activity which at one stage or another had its origins from a biological catalyst. Hence the preservation or construction of the essential activities and chemicals suffices to have the means to give rise to bioluminescent phenomena. Also encompassed are non-naturally occurring luciferases, e.g. a mutated luciferase. Bioluminescent proteins with luciferase activity are thus available from a variety of sources or by a variety of means. Examples of bioluminescent proteins with luciferase activity may be found in U.S. Pat. Nos. 5,229,285; 5,219,737; 5,843,746; 5,196,524; or 5,670,356. Preferred luciferases include *Renilla* luciferase, firefly luciferase and *Gaussia* luciferase.

In a particular embodiment, a sensor of the invention comprises the previously described NanoLuc™ Luciferase (Nluc), a 19.1 kDa, monomeric, ATP independent enzyme that utilizes a novel substrate to produce high intensity, glow-type luminescence. See WO 2012/061530 and Hall et al. ACS Chem Biol. 2012; 7(11):1848-57. The enzyme was generated using directed evolution from a deep-sea shrimp luciferase, creating a luciferase that is much brighter than other forms of luciferase, including both firefly (*Photinus pyralis*) and *Renilla reniformis*. The high intensity luminescence of the NanoLuc enzyme combined with low autoluminescence of the furimazine substrate allows the sensitive detection of low levels of luciferase.

In a sensor molecule of the invention, the luciferase enzyme is fused to a binding protein (BP) capable of binding to the analyte of interest, as well as to the intramolecular ligand L. BP can be a naturally or a non-naturally occurring proteinaceous binding partner of the analyte. In one embodiment, it is a naturally occurring binding partner or functional fragment thereof. Also encompassed are engineered mutants of naturally occurring binding proteins, e.g. through circular permutation, or fragments thereof.

As is illustrated by the Examples herein below, specific embodiments of the invention include sensor molecules wherein BP is a naturally occurring receptor, enzyme, binding protein or fragment thereof.

In another embodiment, BP is a specifically designed non-naturally occurring binding partner of the analyte. Methods are known in the art to provide a binding protein for a given analyte of interest. For example, phage display technology allows for the rapid screening of binding protein candidates from libraries containing randomized peptide sequences. For example, binders of small molecules have been selected from randomized libraries of the anticalin scaffold using phage display (Skerra FEBS J. 2008 June; 275(11):2677-83). Many alternative scaffolds such as thioredoxin A, DARPins, monobodies, affibodies, antibodies, single chain variable fragments (scFv) of antibodies, and others have been developed and can equally be used. The same is true for selection techniques where examples for alternatives to phage display include ribosome, yeast, mRNA, or bacterial display as well as yeast-2-hybrid and yeast-3-hybrid systems.

As another alternative, BP is a computationally designed binding protein. For example, general computational methods have been described in the art for designing proteins that bind to specific ligands. See Fleishman et al. Science 2011; 332(6031):816-21 and Tinberg et al. Nature 2013 (in press). For example, a sensor is provided wherein BP is the computationally designed digoxin binding protein DIG10.3 (Tinberg et al. Nature 2013 (in press)), which sensor is suitably used for detection of digoxin, digoxigenin or another DIG10.3 ligand For example, a sensor is provided wherein BP is a (circularly permuted) dihydrofolate reductase (DHFR), which sensor is suitably used for detecting methotrexate or other DHFR inhibitors.

As another example, BP is a carbonic anhydrase enzyme or fragment thereof, such that the sensor can detect carbonic anhydrase inhibitors, preferably topiramate (brand name Topamax) which is an anticonvulsant (anti-epilepsy) drug.

In yet another example, BP is FK506 binding protein (FKBP) to detect the immunosuppressant molecule rapamycin, or the related macrolide tacrolimus (originally designated FK506), which are used in treating patients after organ transplant, patients suffering from autoimmune disorder, as well as cancer patients.

In yet another example, BP is a (circularly permuted) cyclophilin A to detect the immunosuppressant molecule cyclosporine which is used in treating patients after organ transplant, and patients suffering from autoimmune disorder.

The relative order of Luc and BP within the fusion protein is such that it allows for a high BRET efficiency between Luc and the fluorophore acceptor when the sensor is in the closed state, i.e. when the internal ligand L is bound to BP and for low RET efficiency between Luc and the synthetic fluorophore when the sensor is in the open state. However, a functional sensor does not necessarily show a decrease in RET efficiency upon sensor opening but it could also be the inverse as long as there is an absolute change upon sensor opening. Typically, BP is situated at the terminus of the sensor molecule, while L is present at the other terminus. However, the optimal order of the BP, Luc and the attachment site for the specific attachment of the synthetic regulatory molecule will depend on the structure of the BP, in particular the spatial arrangement of the termini of the BP relative to the ligand binding site. In one embodiment, BP is fused via its N-terminus to Luc. However, if the geometry of BP is such that its N-terminus is at higher distance from the ligand/analyte binding site than its C-terminus, the order of the fusion protein can be reversed to achieve a closer proximity between Luc and fluorophore in the closed state. Thus, also provided is a sensor molecule wherein BP is fused via its C-terminus to Luc. Fusion of Luc to BP can be direct or indirect e.g. via a linker sequence. The polypeptide sequence can be a natural or an unnatural sequence. Typically, the spacing between Luc and BP is 0-10, preferably 0-4 amino acids, The proteinaceous moiety comprising Luc and BP is tethered to a synthetic regulatory molecule. Preferably, the synthetic regulatory molecule is tethered to the proteinaceous moiety in a site-specific fashion to ensure a single, homogenous product. The site of attachment can be chosen among any part of the proteinaceous moiety, i.e. the Luc, the BP or any other (linker) sequence present. The site of attaching the synthetic regulatory molecule to the proteinaceous moiety is chosen such that it allows for a BRET signal change when the sensor molecule switches between the open and closed conformation. In one embodiment, the synthetic molecule is tethered to the N-terminus of Luc, such that the order is (regulatory synthetic molecule)-Luc-BP.

Site-specific attachment of the synthetic regulatory molecule can be achieved by methods known in the art. For example, an amino acid (natural or non-natural) showing a unique reactivity is suitably used. Suitable amino acids include cysteine and any (unnatural) amino acid that allows for a site-specific chemical conjugation reaction, such as click-chemistry, of an appropriate synthetic regulatory molecule. For example, the unnatural amino acid azidohomoalanine (AHA) can be used.

In another embodiment, the synthetic regulatory molecule is site-specifically tethered to the proteinaceous moiety by means of a protein labelling tag. Preferably, the protein labelling tag is a self-labelling protein known in the art, such as SNAP-tag, CLIP-tag or Halo-Tag, and wherein the synthetic regulatory molecule is tethered via the appropriate reactive group. In one embodiment, the self-labeling protein tag is based on a human O6-alkylguanine-DNA-alkyltransferase (hAGT) to which the synthetic regulatory molecule is tethered via a reactive group for hAGT. For example, the protein tag is a SNAP-tag or CLIP-tag. Preferably, the reactive group is a O6-benzylguanine (BG), O4-benzyl-2-chloro-6-aminopyrimidine (CP) or O2-benzylcytosine (BC) derivative. In another embodiment, the self-labeling protein tag is based on a modified haloalkane dehalogenase to which the synthetic regulatory molecule is tethered via a chloroalkane (Halo-Tag).

Alternatively, the protein labelling tag can be a tag that is labelled with the synthetic regulatory molecule through the action of an enzyme, such as sortase (and mutants thereof), lipoic acid ligase (and mutants thereof), biotin ligase (and mutants thereof), phosphopantetheine transferase (PPTase; and mutants thereof). Labeling can be achieved by directly transferring a molecule carrying the synthetic regulatory molecule to the protein tag or by a two-step procedure where in the first step a molecule comprising a bioorthogonal group is attached and in the second step the bioorthogonal group is reacting with the synthetic regulatory molecule comprising an appropriate functional group. For example, enzymatic transfer of a modified phosphopantetheine derivative carrying the synthetic regulatory molecule results in labeling of a specific serine within a certain peptide sequence derived from acyl carrier proteins and thus allows the synthetic regulatory molecule to be linked at exactly one residue present in the protein (see N. George et al. *J Am Chem Soc.* 2004 126, 8896). ACP-tag and MCP-tag are such sequences derived from acyl carrier protein. The presence of the phosphopantetheine transferase is required for the formation of a covalent link between the ACP-tag or MCP-tag and their substrates, which are derivatives of Coenzyme A (CoA). In the labeling reaction, the group conjugated to CoA is covalently attached to the ACP-tag or MCP-tag by the phosphopantetheine transferase. An example for the two-step strategy would be a labeling in which in the first step, a mutant of lipoic acid ligase (LplA) ligates a transcyclooctene derivate onto a LplA acceptor peptide which is part of the sensor molecule. In the second step, ligated trans-cyclooctene is chemoselectively derivatized with a synthetic regulatory molecule conjugated to a tetrazine. Details of such a two step procedure are described by Liu et al. (J Am Chem Soc. 2012 Jan. 18; 134(2):792-5).

Alternatively, the synthetic regulatory molecule is site-specifically tethered to the proteinaceous moiety by means of intein-based labeling. For example, the use of so-called expressed protein ligation (T. Muir, Annu. Rev. Biochem. 2003. 72:249-289) would entail expressing the proteinaceous moiety as fusion protein with a C-terminal intein and the subsequent isolation of the corresponding C-terminal thioester. This thioester is then reacted with a cysteine residue to which the synthetic regulatory molecule is attached, resulting in formation of functional sensor molecule. In split-intein-based protein labeling (Volkmann G, Liu X-Q (2009) PLoS ONE 4(12): e8381), the proteinaceous part of the sensor molecule can be expressed as a fusion protein with a C- or N-terminal split intein. Addition of an appropriate synthetic peptide that represents the other part of the split intein and that also carries the synthetic regulatory molecule results in formation of functional intein, the subsequent excision of the intein from the protein and formation of a functional sensor molecule (Volkmann G, Liu X-Q (2009) PLoS ONE 4(12): e8381)

Preferably, the site of specific attachment of the synthetic regulatory molecule in the sensor molecule is connected via a proteinaceous linker moiety to the other parts of the proteinaceous moiety. The linker moiety can be an artificial polypeptide sequence or a naturally occurring protein designed to ensure sufficient distance between the synthetic regulatory molecule and the luciferase enzyme in the open state of the sensor.

Poly-L-proline linkers can be used as precise molecular rulers due to their well-defined property of forming a stable and rigid helical structure (the polyproline II helix) with a pitch of 3.1 Å per residue in aqueous solution. Accordingly, the linker moiety is preferably a helical linker rich in prolines, which leads to structural rigidity and isolation of the synthetic regulatory molecule from the attached luciferase. Very good results were obtained with a poly-L-Proline linker consisting of at least 15 Pro residues, for instance $Pro_{15}$, or $Pro_{30}$ or even longer. Brun et al. (2011) investigated polyproline linkers of varying length (0, 6, 9, 12, 15, 30, 60) that were inserted between SNAP- and CLIP-tag in the conventional Snifit-sensors. It was found that a length of 30 or 60 proline residues yielded an improved maximum ratio change of the sensor. Accordingly, in one embodiment the linker moiety consists of a poly-L-Pro linker comprising at least 15, preferably at least 20, more preferably at least 30, residues.

The synthetic regulatory molecule comprises a ligand (L) capable of intramolecular binding to BP, and a fluorescent acceptor that can accept the energy from the Luc when they are in spatial proximity. Typically, L is situated at the free end of the regulatory molecule to allow for efficient interaction with BP. Preferably, the relative order of the sensor components is such that the synthetic regulatory molecule is as far away as possible from the luciferase in the open state of the sensor. The design and manufacture of the synthetic regulatory molecule can essentially be performed according to what has been described in the art on conventional FRET-based Snifits. See for example Brun et al. J Am Chem Soc. 2009; 131(16):5873-84; Brun et al. J Am Chem Soc. 2011; 133(40):16235-42; Brun et al. J Am Chem Soc. 2012; 134(18):7676-8.

The fluorescent acceptor molecule is chosen to function as BRET pair together with the luciferase i.e. to accept the bioluminescence energy from Luc in the presence of an appropriate Luc substrate. Furthermore, the fluorescent acceptor molecule is adapted to emit light after accepting the bioluminescence. The choice depends on luciferase emission spectrum and/or application of the sensor molecule. Suitable fluorescent acceptors to form a BRET pair include any fluorophore whose excitation spectra at least partially overlaps with the emission spectra of the respective luciferase. Tetherable fluorophores that can be used as luminescence acceptors in a sensor molecule of the invention include Alexa Fluor dyes, in particular Alexa Fluor 488, Alexa Fluor 594; cyanine dyes such as Cy3, Cy3.5, Cy5, Cy7 and derivatives thereof, in particular sulfonated derivatives; SYTO dyes; SYBR dyes, Bodipy dyes; fluorescent proteins such as EGFP and mCherry; Atto Dyes such as Atto647N; rhodamine dyes such as carboxy-tetramethylrhodamine (TMR), Texas Red, silicon rhodamine; fluorescein derivatives such as carboxyfluorescein and FITC; Oregon Green; triarylmethane dyes as malachite green; naphthalimide dyes such as Lucifer Yellow; xanthene dyes such as SNARF-1; acridine dyes such as acridine orange; coumarins; IRDye stains such as IRDye 700DX. Very suitable acceptors include Cy3 and TMR.

As will be appreciated by the skilled person, a sensor molecule according to the invention can be designed for the detection of any analyte of interest by choosing the appropriate pair of binding protein and intramolecular ligand. The affinity of the ligand for the binding protein has to be sufficiently strong for the sensor molecule to be in its closed state in the absence of free analyte, if binding of ligand and analyte to binding protein are mutually exclusive. If binding of ligand and analyte to binding protein are cooperative, the affinity of the ligand for the binding protein has to be sufficiently strong for the sensor molecule to be in its closed state in the presence of free analyte. In one embodiment, the strength of interaction between binding protein and ligand is characterized by an equilibrium dissociation constant (Kd) of up to 100 µM, preferably up to 50 µM, more preferably up to 10 µM.

For example, the analyte of interest is a drug, a metabolite, a protein, a biomarker, or a nucleic acid molecule. In a preferred embodiment, the analyte is a drug, precursor or metabolite thereof. Blood, serum or plasma drug concentrations may be advantageously measured using a sensor of the invention in various clinical settings e.g. to monitor therapy, confirm a diagnosis of poisoning in hospitalized patients or even to assist in a medicolegal death investigation.

In one embodiment, a sensor for detecting an anti-cancer drug, such as methotrexate, or an immunosuppressant drug, such as rapamycin, or an antibacterial drug such as trimethoprim, or a drug used to treat heart conditions such as digoxin, or an anti-convulsive drug such as topiramate is provided.

In another embodiment, the analyte of interest is a biomarker. As used herein, a biomarker, or biological marker, is an indicator of a biological state, or the past or present existence of a particular type of organism. Biomarkers can be objectively measured and evaluated using a sensor of the invention as indicators of normal biological processes, pathogenic processes, or pharmacologic responses to a therapeutic intervention.

As will be appreciated by the skilled person, a sensor molecule according to the invention can be designed for the detection of any analyte of interest In a first specific aspect, the sensor comprises human carbonic anhydrase (HCA) as BP, preferably in combination with 4-(aminomethyl)benzenesulfonamide or variant thereof as intramolecular ligand. As is demonstrated in FIG. 1, this sensor is advantageously used for the analysis of topiramate (Topamax) or any other HCA ligand.

In a second specific aspect, the invention provides a sensor molecule wherein BP is dihydrofolate reductase (DHFR) or a circularly permuted variant thereof. Preferably, the BP is used in combination with trimethoprim, methotrexate, or variant thereof as intramolecular ligand. As is demonstrated in FIG. 2, this sensor is advantageously used for the analysis of methotrexate, trimethoprim or another DHFR ligand.

In a third aspect, the invention provides a sensor molecule wherein said BP is computationally designed digoxin-binding protein DIG10.3, preferably in combination with progesterone or variant thereof as intramolecular ligand. As is demonstrated in FIG. 3, this sensor is advantageously used for the analysis of digoxin, digoxigenin or another DIG10.3 ligand.

In a fourth specific aspect, the sensor molecule comprises FK506 binding protein (FKBP), preferably in combination with trimethoxyphenyl prolinamide benzanilide or variant thereof as intramolecular ligand. As is demonstrated in FIG. 4, this sensor is advantageously used for the detection of FK506 (tacrolimus), rapamycin or another FKBP ligand.

In yet a further aspect, the sensor molecule comprises cyclophilin A (CypA) or a circularly permuted variant thereof as BP, preferably in combination with ethyl 5-(p-aminobenzyl)-hydantoate, cyclosporine A, or variant thereof as intramolecular ligand. Such sensor finds its use in detecting cyclosporin A or any other CypA ligand.

The invention also relates to a method for providing a sensor molecule of the invention. As is illustrated in Examples 1-4, the proteinaceous moiety and the synthetic regulatory molecule (or precursor thereof) are typically produced as separate entities, after which the synthetic molecule is tethered to the proteinaceous molecule using the appropriate coupling reaction. Hence, the method comprises the steps of providing the proteinaceous moiety and the synthetic regulatory molecule or precursor thereof, and assembling both to yield the sensor molecule.

The proteinaceous moiety can be prepared using standard recombinant DNA techniques well known to those skilled in the art. For example, the BP coding sequence can be genetically introduced into the multiple cloning site of a bacterial expression vector comprising a luciferase sequence such that the BP sequence is operatively linked to the Luc coding sequence. Other proteinaceous components, like a protein labeling tag and/or linker sequences, can also be incorporated using standard techniques. The DNA constructs for various configurations of the proteinaceous moiety of a BRET sensor of the invention can be transfected/transformed in suitable cell lines (eukaryotic or prokaryotic) for its production. The various configurations of the fusion proteins produced in cells, are then purified or semipurified from the transfected/transformed cells. A convenient procedure to purify a proteinaceous moiety is by affinity chromatography e.g. using a His- and/or Strep-tag engineered in the DNA construct. Standard biochemical techniques can be also used alone or in combination with affinity chromatography to purify to various levels the various fusion proteins. Finally, these purified fusion proteins can be also chemically or enzymatically modified before their tethering to the synthetic regulatory molecule.

In another embodiment, the proteinaceous moiety is produced by a combination of in vivo and in vitro methods. First a fusion protein is genetically engineered and expressed in cells using recombinant techniques. The fusion protein is then purified or semi-purified before being modified by chemically or enzymatically attaching a further proteinaceous element, e.g. an element which can serve as a binding protein such as an antibody. Attachment of the further element can be peptide-based or chemically-based.

The synthetic regulatory molecule or precursor thereof can be synthesized by coupling the acceptor fluorophore to the intramolecular ligand, using methods known in the art. The skilled person will understand that the methods used can be selected based on the chemical nature of the fluorophore and/or the ligand. The coupling of acceptor fluorophore to the intramolecular ligand can essentially be performed according to what has been described in the art on conventional FRET-based Snifits. Also, the regulatory molecule or precursor thereof may contain an element which mediates tethering to the proteinaceous moiety. For example, if the synthetic regulatory molecule is to be site-specifically tethered to the proteinaceous moiety of the sensor molecule via a self-labelling protein such as SNAP-tag, CLIP-tag or Halo-Tag, the synthetic regulatory molecule must contain the appropriate reactive group such as a reactive group for hAGT, a O6-benzylguanine (BG), O4-benzyl-2-chloro-6-aminopyrimidine (CP) or O2-benzylcytosine (BC) derivative or a chloroalkane. Reactive groups mediating tethering may be advantageously coupled to the fluorophore acceptor molecule via spacer comprising several polyethylene glycol (PEG) units. For example, a spacer of 10-15 PEG units is suitably used. See for example Brun et al. J Am Chem Soc. 2009; 131(16):5873-84, and the examples herein below.

A regulatory molecule to be used in combination with cysteine or enzyme-mediated coupling can be synthesized based on the examples below, wherein the BG is exchanged with a maleiimide for cysteine coupling, or with a CoA derivative for coupling via phosphopantetheine transferases.

As described herein above, the present inventors observed that the direct use of ratiometric RET sensors for quantification of analytes in complex samples that absorb light at the emission wavelengths of the sensor, e.g. serum or other bodily fluids, is prone to artifacts and leads to unreliable assay outcomes. The inventors hypothesized that the absorbance of sensor-emitted light that would distort the ratio measured can be strongly reduced or even avoided when the distance light has to travel inside the sample is reduced, so that absorbance from sample components does not influence the measured ratio. It was found that this can be achieved by applying the sample to be analyzed to a device (carrier) in which the photons that are emitted from any sensor molecule and that are collected by the detector pass through the sample for a (average) distance shorter than about 330 µm. In particular, the performance of a BRET sensor molecule was significantly increased when the sensor was absorbed to paper. See Example 5 herein below which demonstrates the effect of bilirubin absorbance on the signal emitted from a BRET sensor molecule in solution versus the effect of bilirubin absorbance on the signal emitted from the same sample absorbed to a white paper, However, various other approaches to reduce path lengths are imaginable. For instance, similar advantageous effects can be observed when the sensor is immobilized onto the surface of a glass slide or some other light-transparent support and when the BRET signal is detected through the glass slide after the immobilized sensor is contacted with the sample on the opposite side of the glass slide. Furthermore, similar advantageous effects can be observed when the sample comprising the ratiometric sensor molecule is applied, e.g. as a thin film, onto the surface of a glass slide, and when the BRET signal is detected through either side of the glass slide. The formation of a thin film can be promoted by addition of a surfactant.

Accordingly, the invention also relates to an analytical device comprising a BRET sensor molecule according to any one of the preceding claims, wherein the sensor molecule is arranged in such a manner that, when the device is in use, the photons that are emitted from the sensor molecule and that are collected by the detector pass through the sample for a (average) distance shorter than 330 µm.

In one embodiment, the sensor molecule is immobilized or absorbed to a solid carrier. Preferred carriers include a glass or transparent plastic, a gel and a paper. Preferred carriers are paper and glass sheets. Suitable types of paper include those known in the art as cellulose chromatography papers. For example, Grade 1 Chr world standard chromatography paper sold by Whatman can be used, which has a smooth surface, 0.18 mm thick with a linear flow rate (water) of 130 mm/30 min. It was surprisingly found that a sensor molecule of the invention absorbed (spotted) onto a paper can still be used, e.g. after storage of several weeks at −20 degrees Celcius. This opens up a whole new area of application of the sensors. In particular, a BRET sensor pre-spotted onto a paper can be readily used in a clinical environment, for instance a "bed-side" setting, wherein a bodily fluid sample is subjected to an analysis by the mere application of the sample to the paper comprising immobilized sensor. Preferably, the paper also contains pre-spotted luciferase substrate, such that no other reagents have to be added other than the sample to be tested. In one embodiment, a wax-based printer and a heat source can be used to print microfluidic, hydrophilic paths within the paper, through which flow (drawn by wicking) can be directed to specific "detection zones." See Pollock et al. *Sci Transl Med.* 2012; 4(152):152ra129. It is also possible to stack layers of patterned paper to generate 3D devices. For example, a plasma separation membrane, and a laminated cover of polyester film can be included to protect the device from the environment and limit evaporation. A hole in the lamination cover allows for a fingerstick or pipetted drop (e.g. 30 µl) of whole blood or serum to be applied to the plasma separation membrane. If whole blood is applied, blood cells are captured and retained by the plasma separation membrane while plasma wicks into the individual "zones" in the first layer of paper. In those zones, the plasma fluid reconstitutes dried reagents and generates BRET signal that can be interpreted and quantified.

In one embodiment, the sensor molecule is immobilized to a solid carrier. Immobilization can be covalent or non-covalent and can be achieved using methods known in the art. See for example P. Jonkheijm et al. Angew. Chem. Int. Ed. 2008, 47, 9618-9647.

In one embodiment, the sensor is non-covalently immobilized using a specific ligand/binding moiety pair, such as Biotin/Streptavidin. For example, a biotin moiety or a Strep-tag can be added to the sensor molecule to allow for immobilization on a streptavidin-coated (glass) carrier.

As will be appreciated by the person skilled in the art, a device of the invention is highly suitable as portable, "mix-and-measure" sensors for precise point-of-care quantification of drugs, for example in therapeutic drug monitoring, especially for analyzing complex (biological) samples. In a preferred aspect, the analytical device is or can be handheld, thus allowing for on-site analyte measurements.

Following incubation, the BRET signal can be detected by a simple camera, even a hand-held, camera-equipped Smart-Phone. Thus, also provided is a BRET sensor molecule immobilized or absorbed to a solid carrier wherein the area comprising the immobilized sensor molecule furthermore comprises a luciferase substrate.

The solid carrier approach is however not confined to the novel and improved BRET-based sensor molecules of the invention, but can also be advantageously applied to other quantitative (ratiometric or non-ratiometric) BRET sensors, including those known in the art and those yet to be developed.

The invention therefore also relates to a method for the in vitro detection of an analyte of interest in a sample using bioluminescence resonance energy transfer (BRET), comprising the steps of: (a) contacting the sample with a BRET sensor comprising a bioluminescent donor protein and a fluorescent acceptor as separate entities or a single molecule under conditions allowing for an analyte-induced BRET change to occur and; (b) analyzing energy resonance transfer under conditions wherein at least the BRET sensor or its bioluminescent donor protein (e.g. luciferase) component is immobilized or absorbed to a solid carrier. In one embodiment, the solid carrier is a paper and the light emitted from the paper is detected. In another embodiment, the BRET sensor or its luciferase component is immobilized onto the surface of a glass slide or some other light-transparent support and the BRET signal is detected through the glass slide after the immobilized sensor is contacted with the sample on the opposite side of the glass slide. In another embodiment, the solid carrier is a transparent or non-transparent carrier, e.g. a glass or plastic sheet, and the light emitted by the assay mixture spread out on the glass or plastic surface is measured from the bottom i.e. through the glass or plastic sheet (in the case of a transparent carrier) or either from the bottom or the top (in the case of transparent or non-transparent carriers) of the solid carrier.

As is shown in Example 6, detection of the BRET signal can conveniently performed by a (digital) camera. i.e. by taking the average pixel intensity of the red and blue color channels of each spot.

Preferably, the bioluminescent donor protein has luciferase activity and step (a) is performed in the presence of an appropriate substrate, such as coelenterazine, furimazine (in case of NanoLuc) or a derivative thereof.

Very good results were obtained with a method using a BRET sensor molecule according to the present invention.

The sample can be any sample of biological or artificial origin. In one embodiment, it is a biological sample or a fraction thereof. For example, it is a bodily fluid, preferably selected from the group consisting of blood, serum, saliva, urine, spinal fluid, tears, sperm, sweat, milk. As is clear from the above, a method of the invention is advantageously used for light-absorbing samples, particularly samples that absorb in the blue light region such as a sample containing serum components. A method of the invention is also compatible with very low sample volumes, e.g. volumes of less than five microliters still provide a satisfactory assay outcome. A method for the invention is also advantageously used for the precise quantification of analytes of interest and thus can result in immediate therapeutic actions.

Other applications include (on-site) analysis of waste streams or surface water quality monitoring. For example, in one embodiment the method detects fecal indicator organisms in fresh and marine recreational waters. The analyte of interest can be chosen among the common surface antigens of all fecal coliforms such as core lipopolysaccharide antigens (ethanolamine, specific saccharides, etc.) and glycerol teichoic acids of *E. faecalis* or *E. faecium*, thereby enabling detection across broad ranges of coliform and *Enterococcus* species. Other useful application areas include monitoring indicators of bacterial contamination as bacterial metabolites or signaling molecules for quorum sensing, the quality of control of food, e.g. for vitamins and other nutrients, as well as the presence on toxic compounds or pollutants.

As will be understood, a BRET sensor disclosed herein has many practical applications, which are not limited in any way to carrier-based detection methods. Accordingly, provided is a method for in vitro detecting an analyte of interest in a sample using BRET, comprising the steps of: (a) contacting the sample with a BRET sensor according to the invention in the presence of a luciferase substrate under conditions allowing for an analyte-induced BRET change to occur and; (b) analyzing an energy resonance transfer, wherein a change in emission ratio of luciferase and tethered fluorophore is an indicator of the analyte being present. Step (b) may be performed in solution. Alternatively, e.g. for reasons explained herein above, it can be performed while at least the BRET sensor is immobilized or absorbed to a solid carrier. Thus, in one embodiment the method comprises analyzing an energy resonance transfer while at least the sensor molecule is arranged in such a manner that the photons that are emitted from the sensor molecule and that are collected by a detector pass through the sample for a (average) distance shorter than 330 μm. For example, the sensor molecule is immobilized or absorbed to a solid carrier, preferably a glass or transparent plastic. In a specific aspect, the method employs a physically immobilized sensor. The sample and sensor molecule may be absorbed to a solid carrier or a gel, preferably paper. The method may comprise immobilization or absorption of the BRET sensor and luciferase substrate to a solid carrier, preferably paper, followed by applying at least part of the sample onto a solid carrier comprising sensor and luciferase, and measuring the light emitted by the carrier. The precise order of adding sample, sensor and luciferase substrate can vary depending on specific aims and circumstances. For example, the sensor and the luciferase substrate may be spotted onto and dried on paper and then a sample (e.g. blood plasma) is added. Then, the light signal, i.e. the relative intensities of emission of luciferase and tethered fluorophore, emitted by the paper is measured. Alternatively, the sample and sensor molecule are apart of a thin film, or are confined in a tube, capillary or (microfluidic) chamber. However, the actual assay can be performed in many different ways as is described herein above for the analytical device. Positive and negative control samples can be included, as well as a standard curve.

Also provided is a kit of parts, comprising a sensor molecule according to the invention and a solid carrier. The sensor molecule and the carrier may be present as separate entities, such that the user can immobilize or absorb the sensor prior to use. Alternatively, the sensor is already physically attached to the solid carrier e.g. in the form of pre-spotted paper. The kit finds its use among others in diagnostic methods using a method of the invention. Preferably, the solid carrier is paper or a transparent object, preferably a glass or transparent plastic. The kit may further comprise a luciferase substrate. In case the sensor molecule is based on NanoLuc, the kit preferably comprises furimazine. Other useful ingredients include user's instructions, buffers, materials for sample pretreatment (e.g. lysis buffer), reference samples and compounds for constructing a standard curve.

LEGEND TO THE FIGURES

FIG. 1. (A) Pictorial description of the structure and the sensing mechanism of an exemplary BRET sensor molecule utilising human carbonic anhydrase (HCA) as binding protein; (B) Structure of the synthetic molecule BG-TMR-aminomethylSA. (C) Response curve of the sensor titrated with topiramate in human serum. For details see Example 1.

FIG. 2 (A) Pictorial description of the structure and the sensing mechanism of an exemplary BRET sensor molecule utilising dihydrofolate reductase (DHFR) as binding protein. (B) Structure of the synthetic molecule BG-Cy3-tmp. (C) Schematic description of the difference between wild-type (left) and circularly permuted (right) DHFR. BRET efficiency in the closed state of the sensor can be increased by bringing the fluorophore close to the luciferase using the circularly permuted version. (D) Response curve of the sensor containing wild-type or circularly permuted DHFR titrated with methotrexate. The emission ratio change is more than 10-fold larger in the case of the circularly permuted variant. For details see Example 2.

Figure 3A:
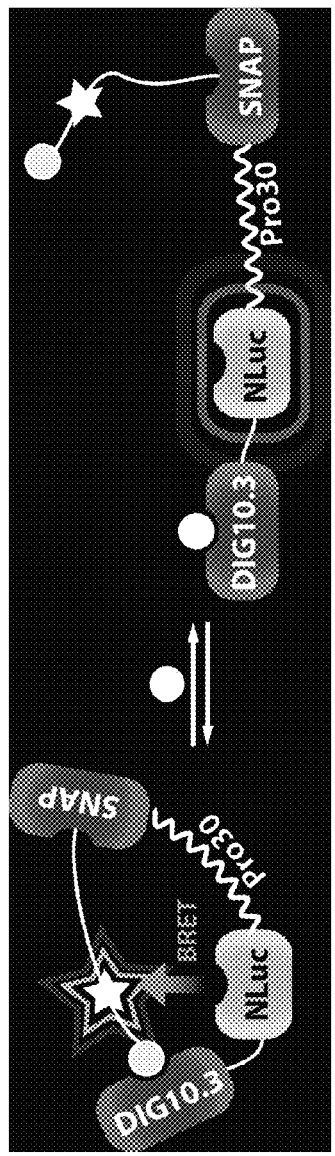

FIG. 3. (A) Pictorial description of the sensor structure and the sensing mechanism of a sensor molecule utilising DIG10.3 as binding protein. (B) Structure of the synthetic molecule BG-TMR-prog. (C) Response curve of the sensor titrated with digoxin in human serum. For details see Example 3.

FIG. 4 (A) Pictorial description of the sensor structure and the sensing mechanism of a sensor molecule utilising FKBP as binding protein. (B) Structure of the synthetic molecule BG-Cy3-fkl. (C) Response curve of the sensor titrated with FK506 in human serum. For details see Example 4.

Figure 5A:
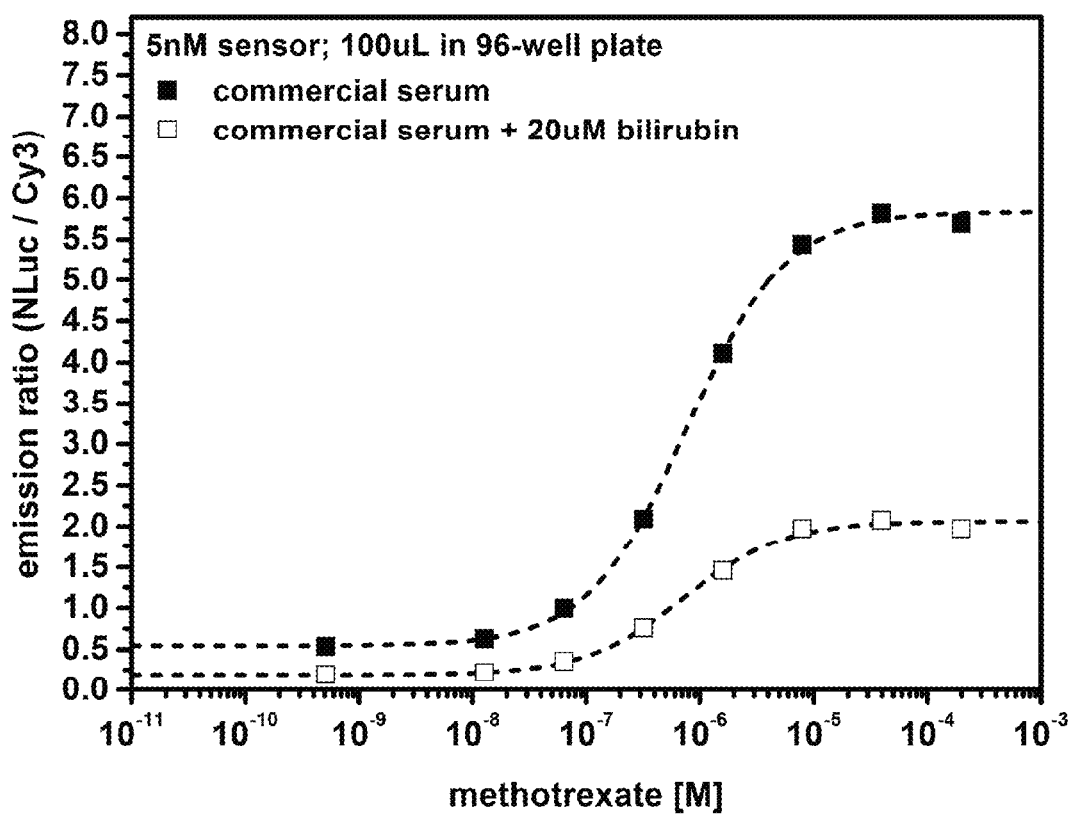
Figure 5B:
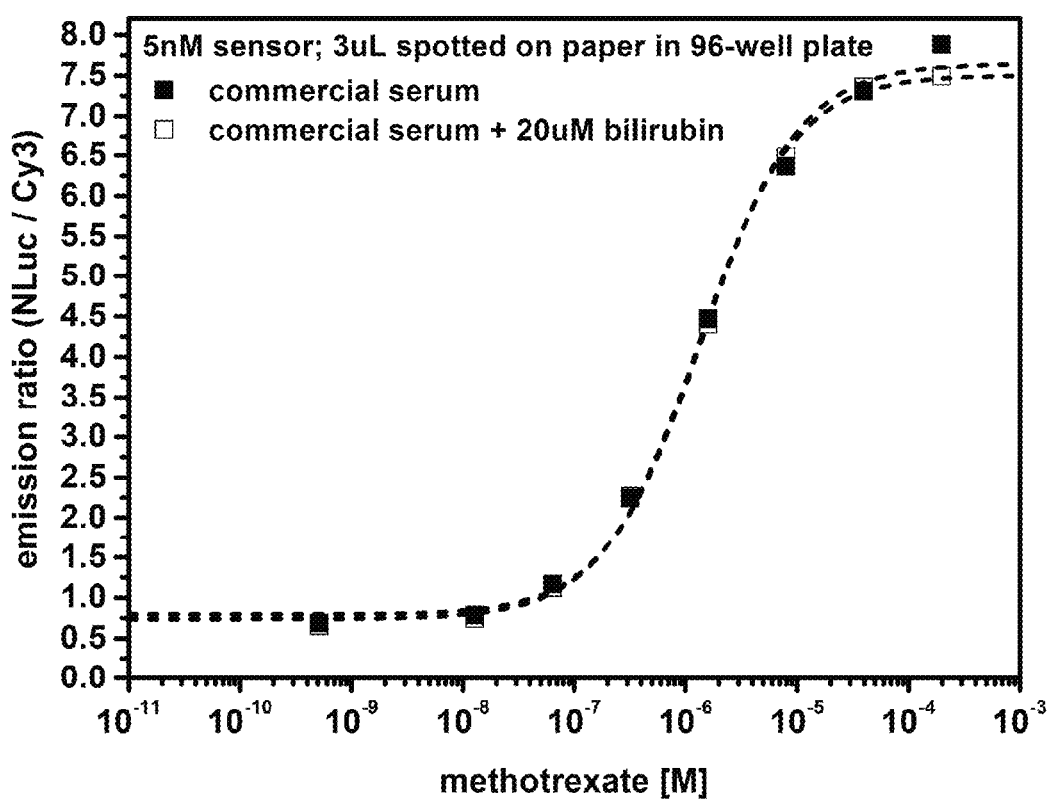

FIG. 5. Effect of serum bilirubin absorbance on the BRET sensor SNAP-Pro30-NanoLuc-DHFRcpL24G5 (A) in solution vs. (B) absorbed to paper. For details see Example 5.

Figure 6A:
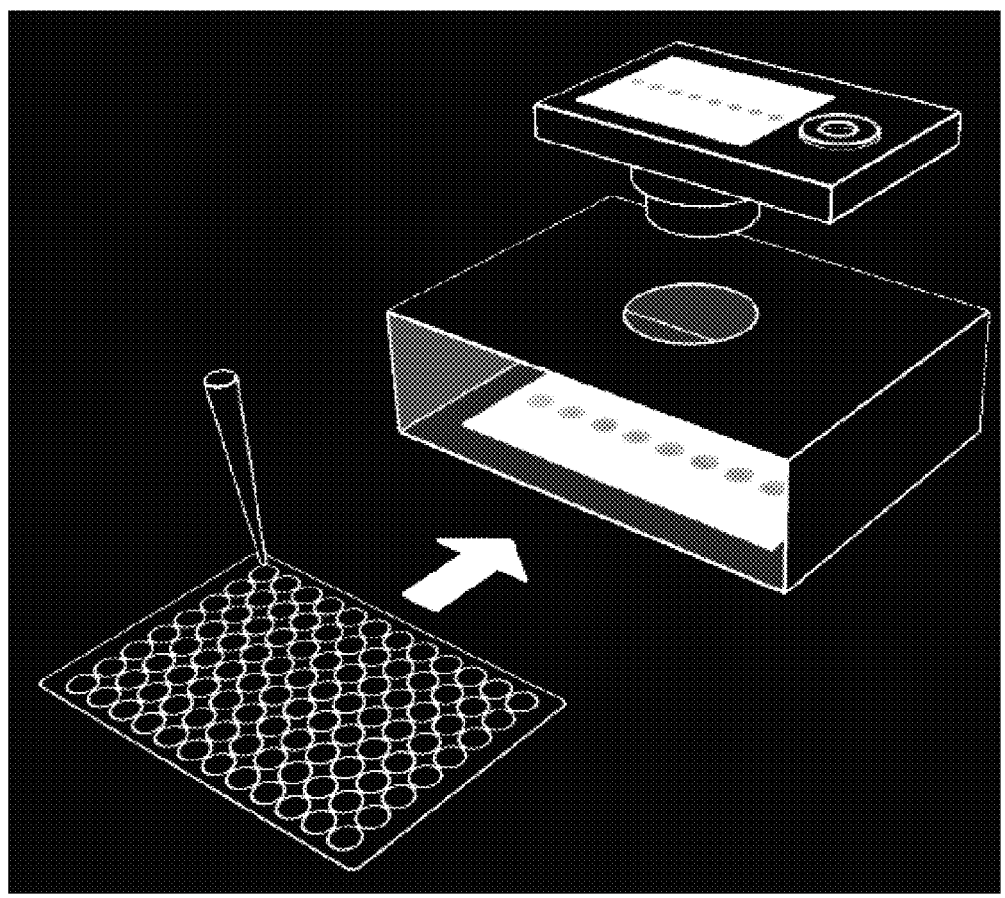

FIG. 6. (A) Schematic description of the experiment outlines in Example 6. (B) Picture taken with a digital camera and histograms of pixel intensity of the red and blue color channels. (C) Response curve of the sensor obtained from the ratio of the average pixel intensities of the blue and red channels.

EXPERIMENTAL SECTION

The Examples below illustrate the design and construction of exemplary BRET-sensors according to the invention and the use thereof in an analytical device or in an analytical method. Reagents and solvents were purchased from Sigma Aldrich (St. Louis, Mo.) or Acros Organics (Waltham, Mass.) and used without further purification. Peptide couplings were performed by activation of the respective carboxylic acid with O—(N-Succinimidyl)-N,N,N,N'-tetramethyluronium tetrafluoroborate (TSTU) or N,N,N',N'-Tetramethyl-O-(1H-benzotriazol-1-yl)uronium hexafluorophosphate (HBTU) in the presence of diisopropylethylamine (DIEA) as base in anhydrous dimethylsulfoxide (DMSO) at room temperature.

Example 1

Topiramate Sensor

This example describes the design and construction of a BRET sensor capable of sensing concentrations of the drug topiramate (Topamax). The sensor comprises human carbonic anhydrase II (HCA) as a binding protein, an aromatic sulfonamide as an intramolecular ligand. Luciferase and TMR form the BRET pair (see FIG. 1A,B).

A synthetic regulatory molecule containing an $O^6$-benzylguanine (BG) group for SNAP-tag labeling, the fluorophore tetramethylrhodamine (TMR), and 4-(aminomethyl)benzenesulfonamide (aminomethylSA) as tethered ligand was synthesized according to Scheme 1.

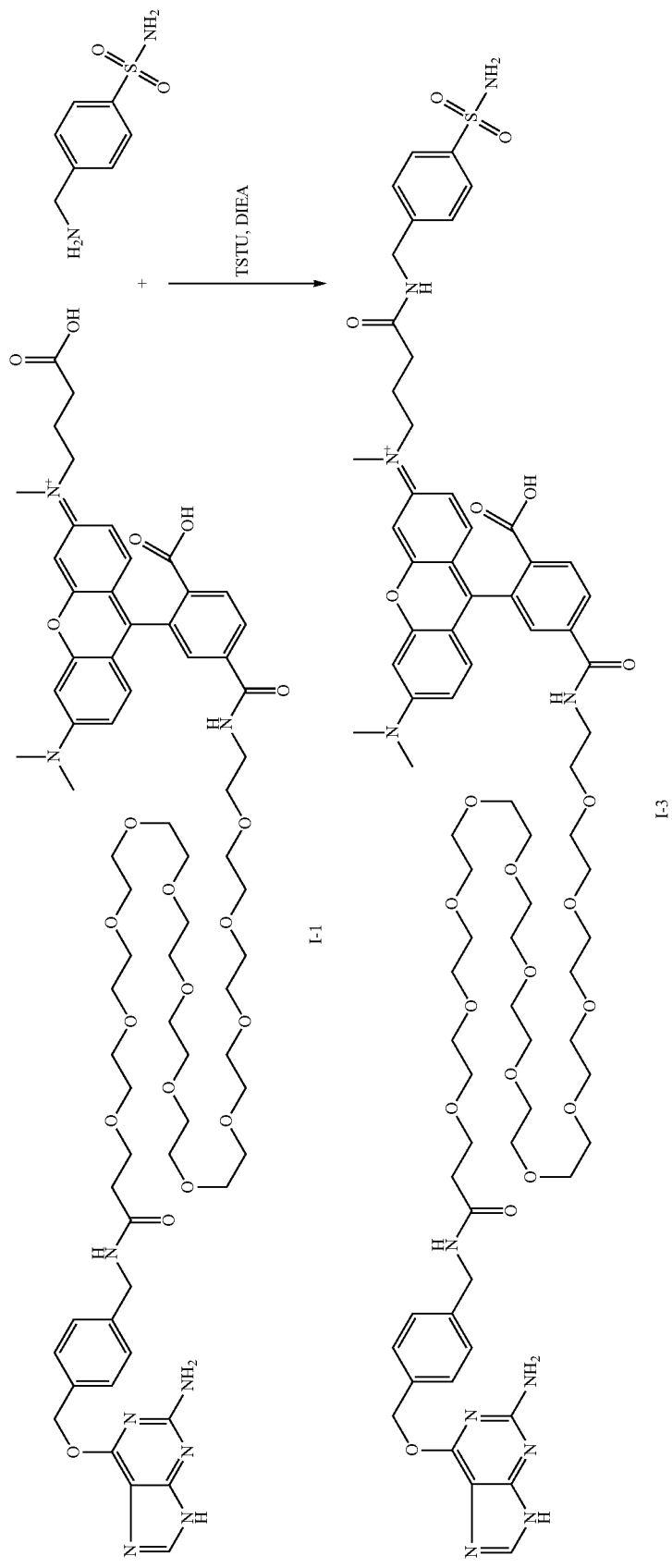
Scheme 1: Schematic representation of the synthesis of the molecule BG-TMR-aminomethylISA.

BG-EG$_{11}$-TMR-COOH (I-1) was prepared as previously described (Brun et al. J Am Chem Soc. 2009; 131(16):5873-84; Kvach et al. Bioconjug Chem. 2009, 20(8), 1673-82) and it was coupled to 4-(aminomethyl)benzenesulfonamide hydrochloride (I-2) to afford the labeling compound BG-TMR-aminomethylSA (I-3).

A fusion protein of SNAP-tag, a 30-proline linker, Nano-Luc luciferase (Promega, Fitchburg, Wis.) and HCA was constructed by replacing the coding sequence of CLIP-tag in the previously described sensor SNAP-PP30-CLIP-HCA (Brun et al. J Am Chem Soc. 2011; 133(40):16235-42) by the coding sequence of NanoLuc luciferase using standard cloning techniques. The fusion protein was expressed in the *E. coli* strain Rosetta-gami and purified using a C-terminal His-tag as well as an N-terminal Strep-tag.

The sensor molecule was assembled by labeling SNAP-tag with the synthetic molecule BG-TMR-aminomethylSA (FIG. 1B). We developed this ligand since those used for our previously described FRET sensors (Brun et al. J Am Chem Soc. 2009; 131(16):5873-84; Brun et al. J Am Chem Soc. 2011; 133(40):16235-42) either were too high in affinity making opening of the sensor more difficult reducing sensitivity, or too weak preventing complete sensor closing in the absence of analyte. The purified protein was diluted to a concentration of 1 µM in HEPES buffer (50 mM HEPES, 50 mM NaCl, pH 7.2) and incubated with a 4-fold molar excess of the synthetic compound BG-TMR-aminomethylSA for 1 hour at room temperature.

To evaluate the response of the BRET sensor to different topiramate concentrations, the assembled sensor molecule was diluted to a concentration of 10 nM in 100 µL normal human serum (Merck Millipore, Billerica, Mass.) containing defined concentrations of topiramate in white non-binding 96-well plates (Greiner Bio-One, Kremsmünster, Austria). The solutions were incubated at room temperature for at least 10 minutes to ensure that the sensor had reached equilibrium. Bioluminescence was measured on an EnVision Multilabel Reader (Perkin Elmer): 5 seconds before the measurement, 100 µL furimazine (Promega, Fitchburg, Wis.) stock diluted 100-fold in HEPES buffer was added into the wells using the instrument's injector and the signal was collected using an emission filter for Umbelliferone (wavelength: 460 nm, bandwidth: 25 nm) to record NanoLuc emission and a filter for Cy3 (wavelength: 595 nm, bandwidth: 60 nm) to record TMR emission.

FIG. 1C shows the response of the sensor to different topiramate concentrations. At low concentrations, the sensor is in its closed conformation, permitting efficient resonance energy transfer from NanoLuc to TMR and leading to a low NanoLuc/TMR emission ratio. At high topiramate concentrations the intramolecular ligand is displaced and the sensor is shifted to an open conformational state. In this state resonance energy transfer from NanoLuc to TMR is inefficient, leading to high NanoLuc/TMR emission ratios. As will be understood by the person skilled in the art, the sensor can also be used for other drugs that bind to HCA, such as ethoxzolamide, acetazolamide and others.

Example 2

Methotrexate Sensor

A BRET sensor capable of sensing the anti-cancer drug methotrexate concentrations was constructed. It is based on a circularly permuted dihydrofolate reductase (DHFR) as a binding protein, trimethoprim as an intramolecular inhibitor, and a luciferase and Cy3 as a BRET pair (see FIG. 2A,B). A molecule containing an O$^6$-benzylguanine (BG) group for SNAP-tag labeling, the fluorophore Cy3 and trimethoprim (tmp) as tethered ligand was synthesized according to scheme 2.

4-Demethyltrimethoprim (II-1) was alkylated with methyl 5-bromopentanoate (II-2) in the presence of anhydrous potassium carbonate in dimethylformamide (DMF). The reaction mixture was then poured in 1 M aqueous sodium hydroxide to give II-3, that was subsequently coupled to ethylene diamine using TSTU as coupling reagent to obtain the trimethoprim derivative II-4. BG-EG11-NH2 (II-6) and Cy3 (II-5) were prepared as previously described Mujumdar et al. Bioconjugate Chemistry 1993, 4, 105-111) and the two building blocks were coupled together with II-4 to give the labeling molecule BG-Cy3-tmp (II-7).

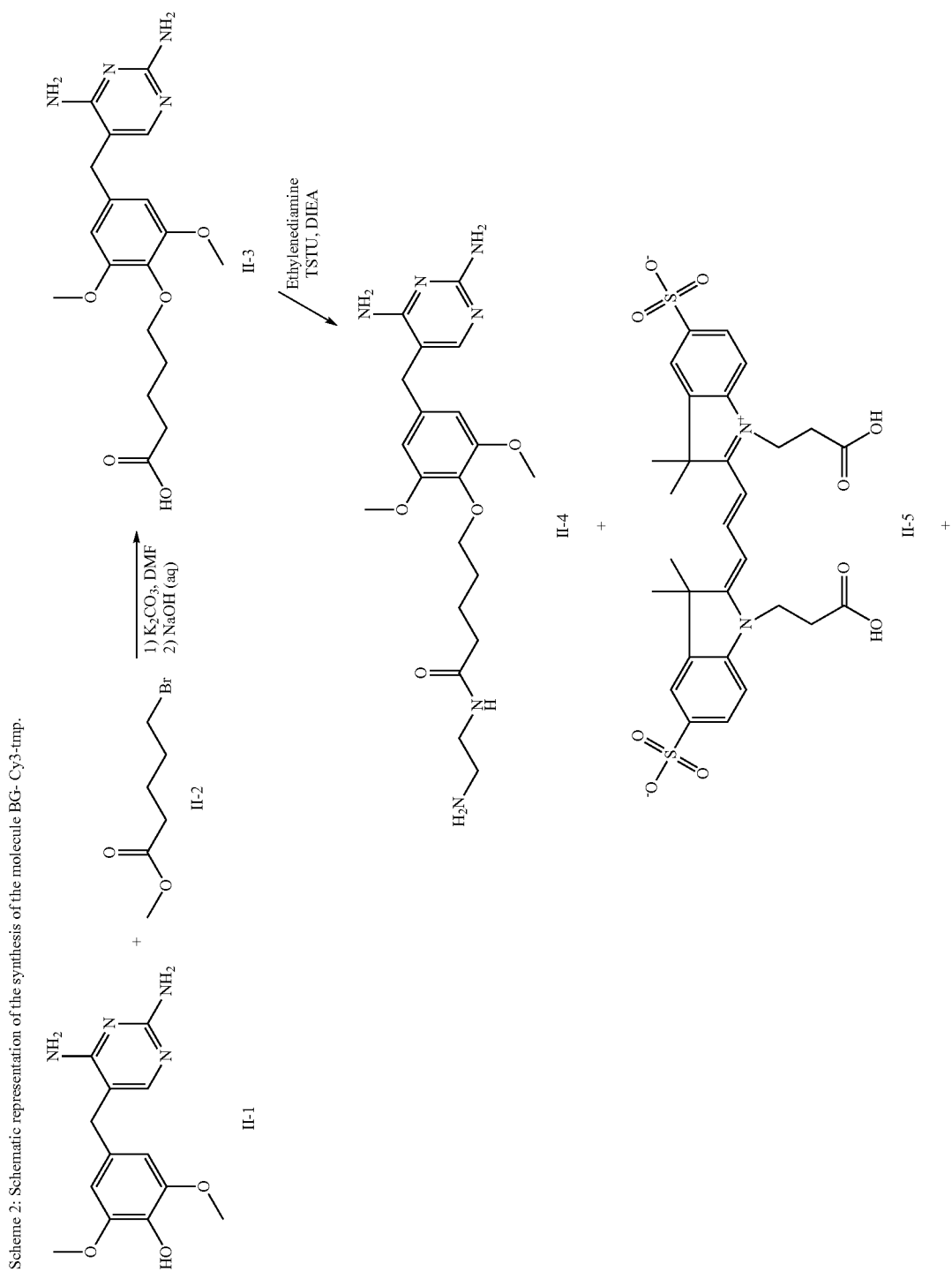
Scheme 2: Schematic representation of the synthesis of the molecule BG-Cy3-tmp.

-continued
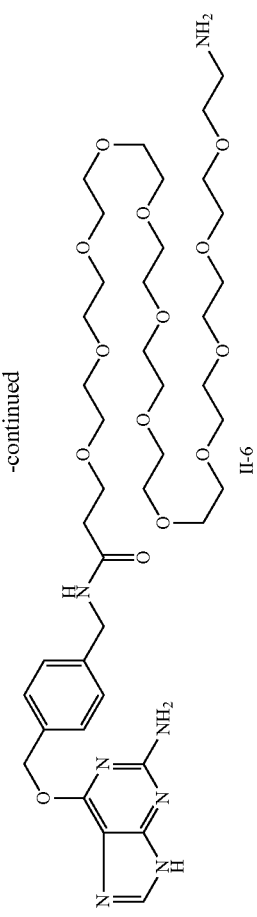
↓ TSTU, DIEA
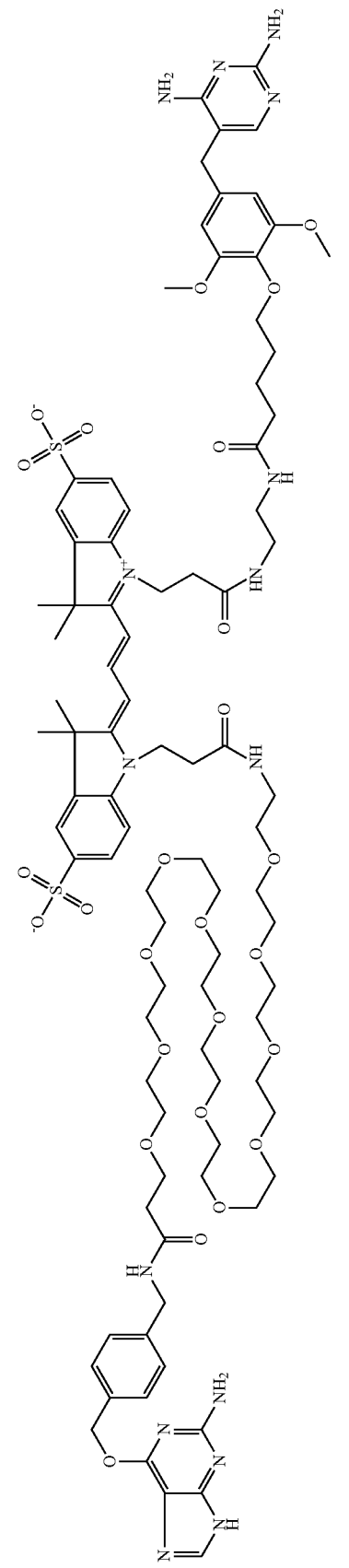

A fusion protein of SNAP-tag, a 30-proline linker, NanoLuc luciferase (Promega, Fitchburg, Wis.) and DHFR was constructed by replacing the coding sequence of HCA in the sensor SNAP-PP30-NanoLuc-HCA (see Example 1) by the coding sequence of either wild-type bacterial DHFR or the previously described DHFR-variant DHFRL24G5 (Brun et al. J Am Chem Soc. 2009; 131(16):5873-84; Iwakura et al. Protein Eng 1998, 11, 707-713), which is circularly permuted between residues Asn23 and Leu24 with a 5-glycine linker connecting the original termini using standard cloning techniques. A circularly permuted variant of DHFR was chosen so that NanoLuc luciferase could be attached closely to the binding site of the intramolecular ligand, bringing it in close proximity to the acceptor fluorophore Cy3 in the closed state of the sensor.

In wild-type DHFR, the termini are far away from the active site which does not allow the construction of a sensor with a high BRET-efficiency in the closed state. The position Asn23, Leu24 on the other hand is in a loop very close to the active site of the protein (see FIG. 2C).

The fusion protein was expressed in the *E. coli* strain Rosetta-gami and purified using a C-terminal His-tag as well as an N-terminal Strep-tag. The sensor molecule was assembled by labeling SNAP-tag with the synthetic molecule BG-Cy3-tmp (FIG. 1B). The purified protein was diluted to a concentration of 1 µM in HEPES buffer (50 mM HEPES, 50 mM NaCl, pH 7.2) and incubated with a 4-fold molar excess of the synthetic compound BG-Cy3-tmp for 1 hour at room temperature.

To test the response to different methotrexate concentrations, the assembled sensor molecule was diluted to a concentration of 10 nM in 100 µL HEPES buffer supplemented with 100 µM NADPH containing defined concentrations of methotrexate in white non-binding 96-well plates (Greiner Bio-One, Kremsmünster, Austria). The solutions were incubated at room temperature for at least 30 minutes to ensure that the sensor had reached equilibrium. Bioluminescence was measured on an EnVision Multilabel Reader (Perkin Elmer): 5 seconds before the measurement, 100 µL furimazine (Promega, Fitchburg, Wis.) stock diluted 100-fold in HEPES buffer was added into the wells using the instrument's injector and the signal was collected using an emission filter for Umbelliferone (wavelength: 460 nm, bandwidth: 25 nm) to record NanoLuc emission and a filter for Cy3 (wavelength: 595 nm, bandwidth: 60 nm) to record Cy3 emission.

Figure 2D:
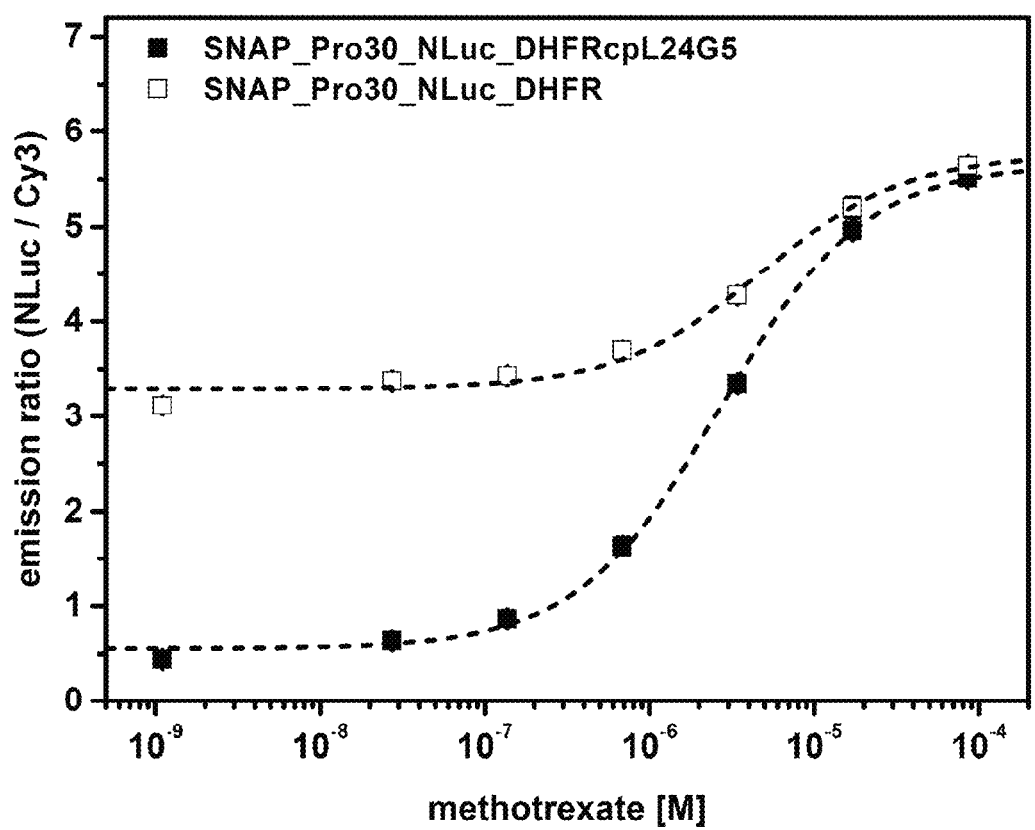

FIG. 2D shows the response of the sensor to different methotrexate concentrations. At low concentrations, the sensor is in its closed conformation, permitting efficient resonance energy transfer from NanoLuc to Cy3 and leading to a low NanoLuc/Cy3 emission ratio. At high methotrexate concentrations the intramolecular ligand is displaced and the sensor is shifted to an open conformational state. In this state, resonance energy transfer from NanoLuc to Cy3 is inefficient, leading to high NanoLuc/Cy3 emission ratios.

As will be understood, the sensor can also be used for other (drug) analytes that bind to DHFR, such as pemetrexed, pyrimethamine, proguanil, trimethoprim, and others.

Example 3

Digoxin Sensor

A BRET sensor capable of sensing digoxin concentrations was constructed. It is based on the computationally designed binding protein DIG10.3 (Tinberg et al. Nature 2013 in press), progesterone as an intramolecular ligand, and a luciferase and TMR as a BRET pair (see FIG. 3 A,B).

A molecule containing an $O^6$-benzylguanine (BG) group for SNAP-tag labeling, the fluorophore tetramethylrhodamine (TMR), and progesterone (prog) as tethered ligand was synthesized according to Scheme 3.

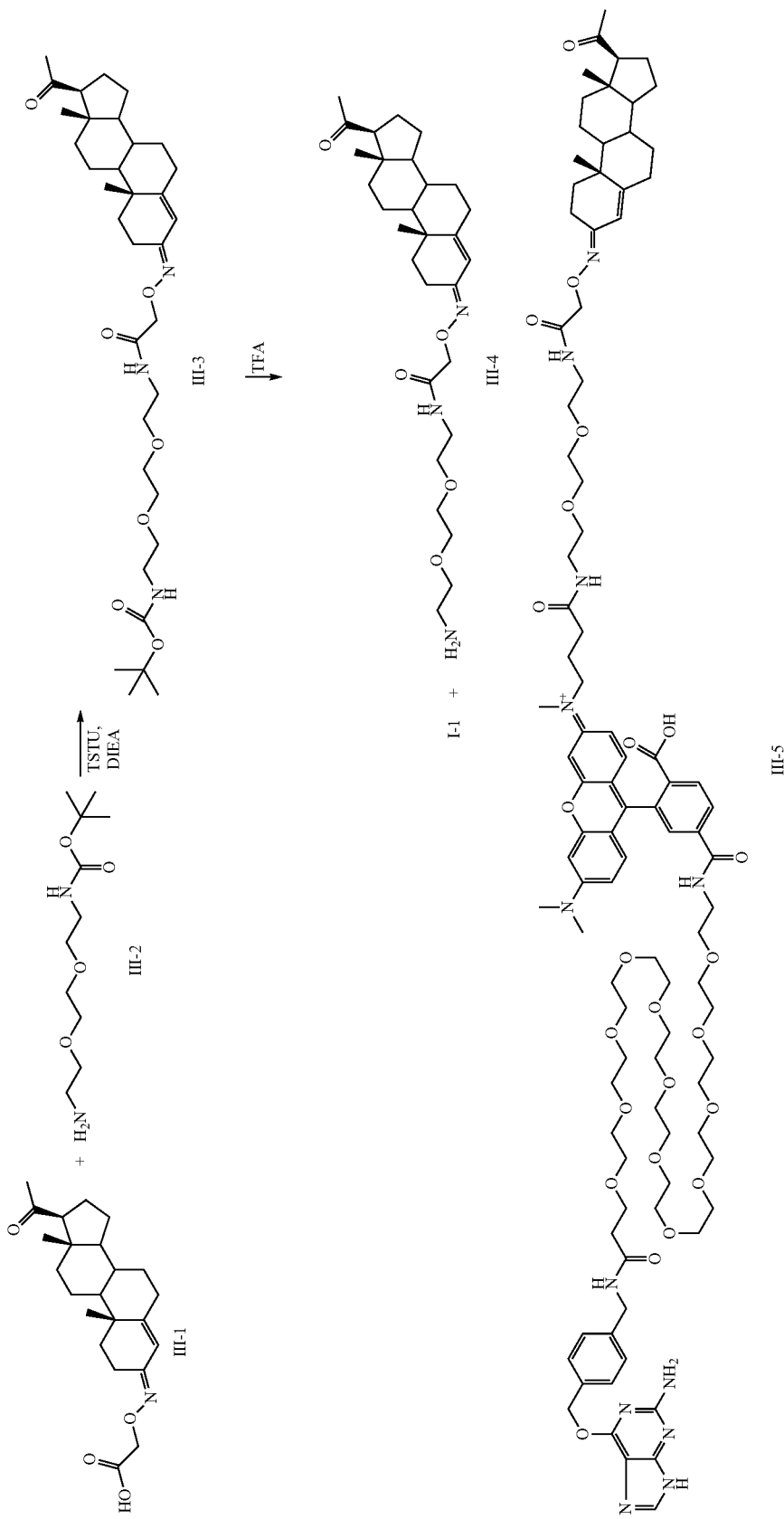

Progesterone-(3-O-carboxymethyl)oxime (III-1) was tethered to a short $PEG_2$ tether by peptide coupling to 1-N-Boc-3,6-dioxa-1,8-diaminooctane (III-2) to give III-3, and the Boc protecting group was then removed by treatment with trifluoroacetic acid (TFA) to afford the amino derivative III-4. BG-$EG_{11}$-TMR-COOH (I-1) was prepared as previously described (Brun et al. J Am Chem Soc. 2009; 131(16):5873-84; Kvach et al. Bioconjug Chem. 2009, 20(8), 1673-82) and it was coupled to (III-4) to afford the labeling compound BG-TMR-prog (III-5).

A fusion protein of DIG10.3, NanoLuc luciferase (Promega, Fitchburg, Wis.), a 30-proline linker and SNAP-tag was constructed using standard cloning techniques. DIG10.3 was fused via its C-terminus since it is located closer to the binding site of the protein. This makes it possible to attach NanoLuc luciferase close to the binding site of the intramolecular ligand, bringing it in close proximity to the acceptor fluorophore TMR in the closed state of the sensor. The fusion protein was expressed in the *E. coli* strain Rosetta-gami and purified using a C-terminal His-tag as well as an N-terminal Strep-tag.

Figure 3B:
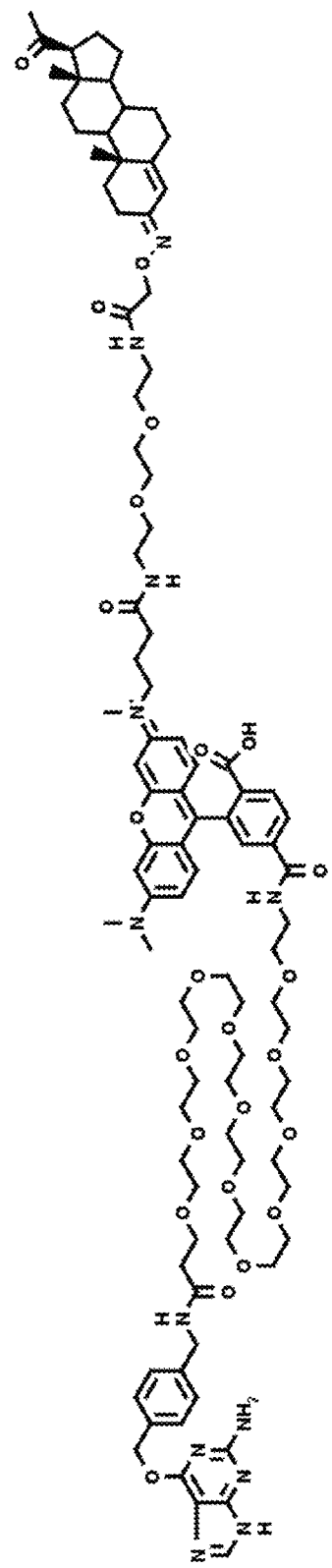

The sensor molecule was assembled by labeling SNAP-tag with the synthetic molecule BG-TMR-prog (FIG. 3B). Progesterone binds weakly to DIG10.3. It thus closes the sensor but still can be easily displaced by digoxin, making the sensor significantly more sensitive than if digoxin were used as a tethered ligand. The purified protein was diluted to a concentration of 1 µM in HEPES buffer (50 mM HEPES, 50 mM NaCl, pH 7.2) and incubated with a 4-fold molar excess of the synthetic compound BG-TMR-prog for 1 hour at room temperature.

To test the response to different digoxin concentrations, the assembled sensor molecule was diluted to a concentration of 10 nM in 100 µL normal human serum (Merck Millipore, Billerica, Mass.) containing defined concentrations of digoxin in white non-binding 96-well plates (Greiner Bio-One, Kremsmünster, Austria). The solutions were incubated at room temperature for at least 10 minutes to ensure that the sensor had reached equilibrium. Bioluminescence was measured on an EnVision Multilabel Reader (Perkin Elmer): 5 seconds before the measurement, 100 µL furimazine (Promega, Fitchburg, Wis.) stock diluted 100-fold in HEPES buffer was added into the wells using the instrument's injector and the signal was collected using an emission filter for Umbelliferone (wavelength: 460 nm, bandwidth: 25 nm) to record NanoLuc emission and a filter for Cy3 (wavelength: 595 nm, bandwidth: 60 nm) to record TMR emission.

Figure 3C:
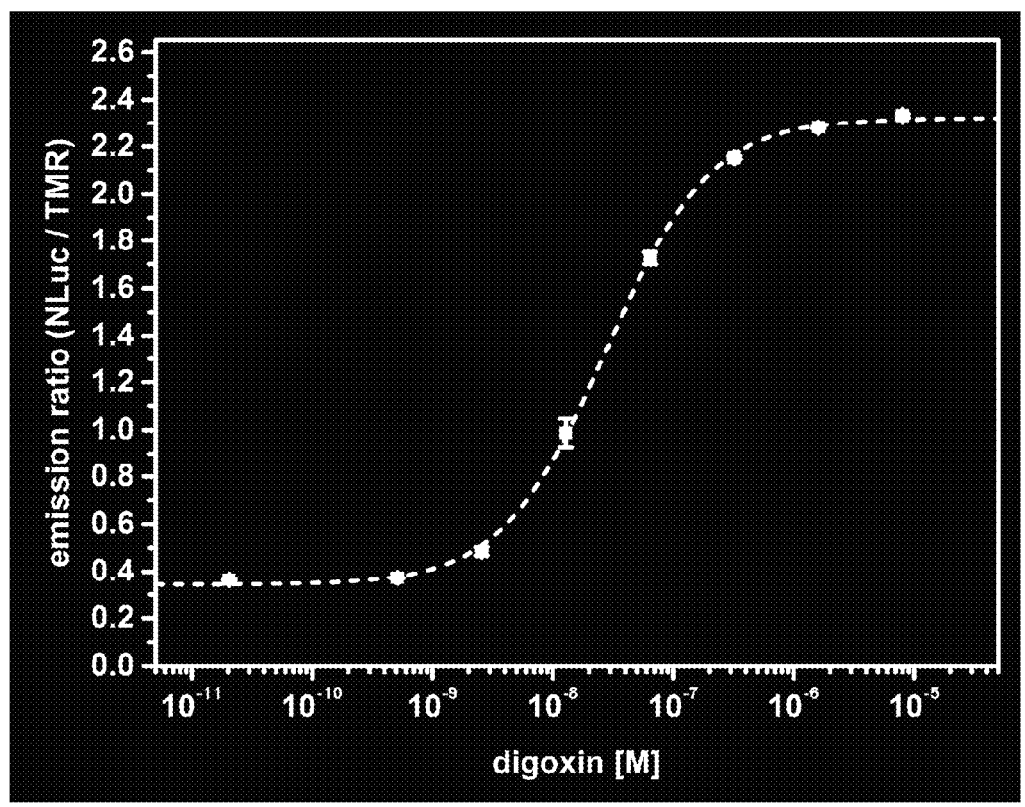

FIG. 3C shows the response of the sensor to different digoxin concentrations. At low concentrations, the sensor is in its closed conformation, permitting efficient resonance energy transfer from NanoLuc to TMR and leading to a low NanoLuc/TMR emission ratio. At high digoxin concentrations the intramolecular ligand is displaced and the sensor is shifted to an open conformational state. In this state, resonance energy transfer from NanoLuc to TMR is inefficient, leading to high NanoLuc/TMR emission ratios.

Example 4

FK506 Sensor

A BRET sensor capable of sensing concentrations of the immunosuppressant molecule FK506 was constructed. It is based on FKBP12 as a binding protein, a bispecific inhibitor for FKBP as an intramolecular inhibitor, and a luciferase and Cy3 as a BRET pair (see FIG. 4A,B).

A molecule containing an $O^6$-benzylguanine (BG) group for SNAP-tag labeling, the fluorophore Cy3 and a bifunctional ligand for FKBP (fkl) as tethered ligand was synthesized according to Scheme 4. The synthetic scheme consists of a convergent synthesis of two site-specific FKBP-ligands, subsequently linked together with a short PEG-linker. According with previously published procedures (Rohrig et al. ChemMedChem 2007, 2, 1054-1070) with some modifications, the first ligand was prepared by coupling with HBTU 4-aminophenol (IV-1) and 4-hydroxybenzoic acid (IV-2) to obtain IV-3. Two different aliquots of triethylene glycol di-p-tosylate (IV-4) were reacted with one equivalent each of potassium phthalimide or sodium azide in DMF to afford IV-5 and IV-6 respectively. IV-3 was subjected to a 2-step alkylation in DMF, using sodium carbonate as base: first one equivalent of IV-5 was added to alkylate the most reactive phenolic group, followed by an excess of IV-6 to perform the alkylation of the second reactive hydroxyl group and obtain IV-7. The phthalimide protecting group was removed using 40% methylamine solution in water and obtain the free amino group in IV-8. The second ligand was prepared separately: 3',4',5'-trimethoxyacetophenone (IV-9) was oxidized using selenium dioxide in pyridine to obtain the acid IV-10, that was coupled with TSTU to proline methyl ester (IV-11) and treated with 1 M aqueous sodium hydroxide to hydrolyze the methyl ester and afford IV-12. IV-8 and IV-12 were coupled using TSTU to give the azido-modified bispecific ligand IV-13. BG-$EG_{11}$-$NH_2$ (II-6) and Cy3 (II-5) were prepared as previously described (Brun et al. J Am Chem Soc. 2009; 131(16):5873-84; Brun et al. J Am Chem Soc. 2011; 133(40):16235-42) and the two building blocks were coupled together with propargylamine to give the alkyne-modified BG-Cy3-alkyne (IV-14). IV-13 was coupled to IV-14 via click-chemistry using copper(II) sulfate, tris[(1-benzyl-1H-1,2,3-triazol-4-yl)methyl]amine and sodium ascorbate in DMSO and afford the labeling compound BG-Cy3-fkl (IV-15).

A fusion protein of SNAP-tag, a 30-proline linker, NanoLuc luciferase (Promega, Fitchburg, Wis.) and FKBP12 was constructed by replacing the coding sequence of HCA in the sensor SNAP-PP30-NanoLuc-HCA (see example 1) by the coding sequence of FKBP12. The fusion protein was expressed in the *E. coli* strain Rosetta-gami and purified using a C-terminal His-tag as well as an N-terminal Strep-tag.

Figure 4A:
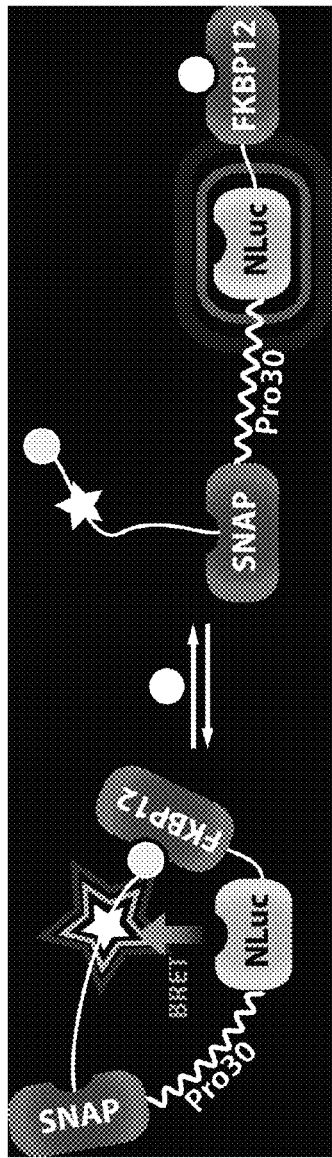
Figure 4B:
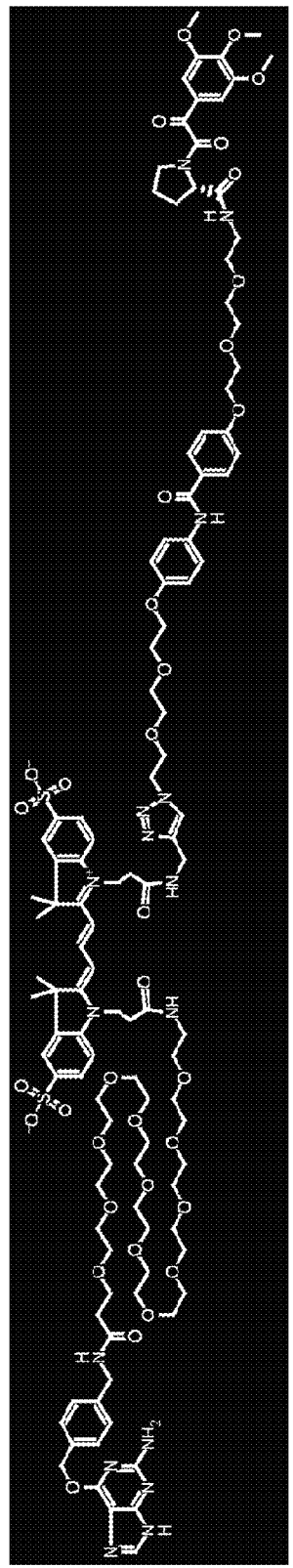

The sensor molecule was assembled by labeling SNAP-tag with the synthetic molecule BG-Cy3-fkl (FIG. 4B). This previously described ligand consists of two parts that bind to two distinct sites on FKBP12. The second part which is directly attached to Cy3 in BG-Cy3-fkl—binds closely to the N-terminus of the protein (Rohrig et al. ChemMedChem 2007, 2, 1054-1070). This brings Cy3 into close promixity of NanoLuc luciferase in the closed state of the sensor permitting efficient BRET. The purified protein was diluted to a concentration of 1 µM in HEPES buffer (50 mM HEPES, 50 mM NaCl, pH 7.2) and incubated with a 4-fold molar excess of the synthetic compound BG-Cy3-fkl for 1 hour at room temperature.

To test the response to different FK506 concentrations, the assembled sensor molecule was diluted to a concentration of 1 nM in 100 µL normal human serum (Merck Millipore, Billerica, Mass.) containing defined concentrations of FK506 in white non-binding 96-well plates (Greiner Bio-One, Kremsmünster, Austria). The solutions were incubated at room temperature for at least 10 minutes to ensure that the sensor had reached equilibrium. Bioluminescence was measured on an EnVision Multilabel Reader (Perkin Elmer): 5 seconds before the measurement, 100 µL 1 µg/mL coelenterazine-h (NanoLight, Pinetop, Ariz.) in HEPES buffer was added into the wells using the instrument's injector and the signal was collected using an emission filter for Umbelliferone (wavelength: 460 nm, bandwidth: 25 nm) to record NanoLuc emission and a filter for Cy3 (wavelength: 595 nm, bandwidth: 60 nm) to record Cy3 emission.

Figure 4C:
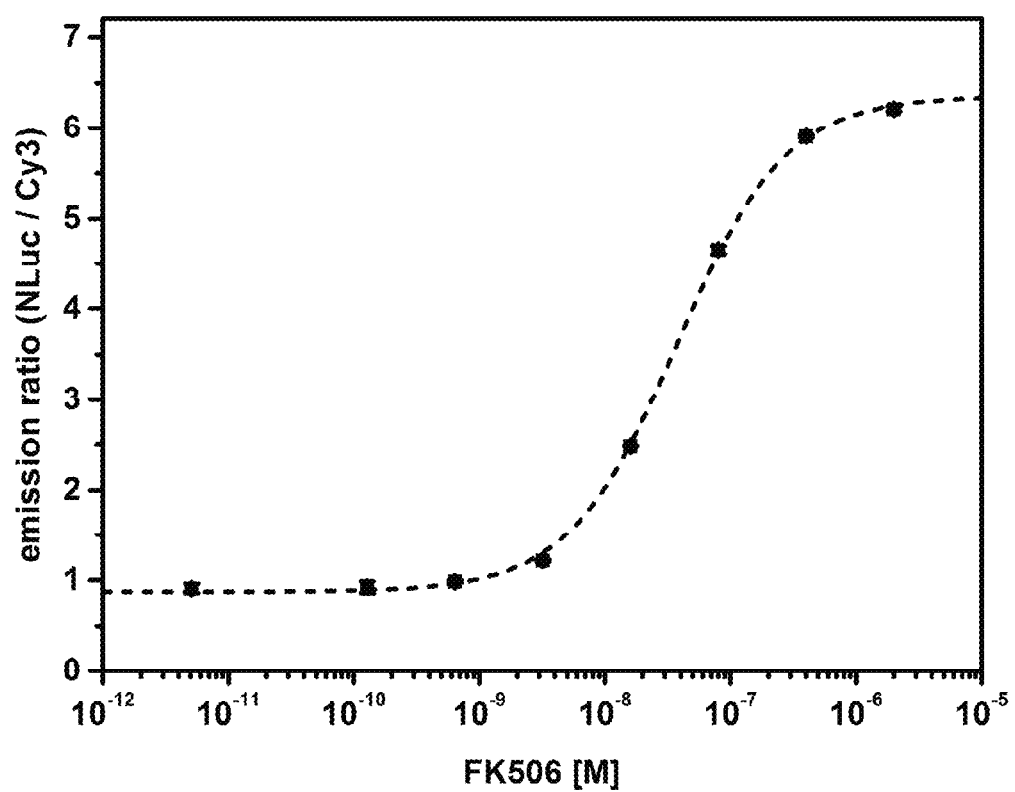

FIG. 4C shows the response of the sensor to different FK506 concentrations. At low concentrations, the sensor is in its closed conformation, permitting efficient resonance energy transfer from NanoLuc to Cy3 and leading to a low NanoLuc/Cy3 emission ratio. At high FK506 concentrations the intramolecular ligand is displaced and the sensor is shifted to an open conformational state. In this state, resonance energy transfer from NanoLuc to Cy3 is inefficient, leading to high NanoLuc/Cy3 emission ratios.

The sensor can of course also be used for other drugs that bind to FKBP12, e.g. rapamycin.

Example 5

Analytical Device Comprising BRET Sensor

This Example demonstrates the surprising advantages of immobilizing or absorbing a BRET sensor to a solid carrier when it is used for the analysis of a sample which absorbs in the blue light region. To test the effect of different concentrations of bilirubin in human serum, we chose the methotrexate sensor SNAP-Pro30-NanoLuc-DHFRcpL24G5 (see Example 2) as representative example for preparing an analytical device. The titration of the BRET sensor with methotrexate was performed in normal human serum with and without the addition of 10 µM bilirubin.

The sensor molecule was assembled as described in Example 2. It was diluted to a concentration of 10 nM in 50 µL normal human serum supplemented with no or 20 µM bilirubin and containing defined concentrations of methotrexate in white non-binding 96-well plates (Greiner Bio-One, Kremsmünster, Austria). The solutions were incubated at room temperature for at least 10 minutes to ensure that the sensor had reached equilibrium. To start the bioluminescence reaction, 50 µL furimazine (Promega, Fitchburg, Wis.) diluted 50-fold in HEPES buffer (50 mM HEPES, 50 mM NaCl, pH 7.2) was added to each well. 3 µL from each well was then spotted onto pieces of Whatman No. 1 chromatography paper (GE Healthcare, Little Chalfont, United Kingdom) that were produced using a standard hole punch and put into empty wells of the same 96-well plate. Bioluminescence from both the wells containing solutions and those containing paper was measured on an EnVision Multilabel Reader (Perkin Elmer): the signal was collected using an emission filter for Umbelliferone (wavelength: 460 nm, bandwidth: 25 nm) to record NanoLuc emission and a filter for Cy3 (wavelength: 595 nm, bandwidth: 60 nm) to record Cy3 emission.

FIG. 5A shows the response of the sensor in solution to different methotrexate concentrations in the presence and in the absence of additional 10 µM bilirubin. Clearly, bilirubin strongly absorbs blue light leading to a decreased NanoLuc/Cy3 (blue light/red light) emission intensity ratio. Since the concentration of bilirubin varies substantially between samples of human serum, the sensor cannot be used in this way to measure analyte concentrations. In contrast, when the sensor is spotted on paper, the effect of the bilirubin is not observed anymore as is shown in FIG. 5. We speculate that the reason for this is the fact, that the light path of the signal in the sample is significantly reduced.

Example 6

BRET Detection Using a Camera

To demonstrate the detection of the BRET-sensor response using a simple digital camera, we chose the methotrexate sensor SNAP-Pro30-NanoLuc-DHFRcpL24G5 (see Example 2) as an example.

The sensor molecule was assembled as described in Example 2. It was diluted to a concentration of 100 nM in 50 µL normal human serum spiked with defined concentrations of methotrexate. The solutions were incubated at room temperature for at least 10 minutes to ensure that the sensor had reached equilibrium. To start the bioluminescence reaction, 50 µL furimazine (Promega, Fitchburg, Wis.) diluted 50-fold in HEPES buffer (50 mM HEPES, 50 mM NaCl, pH 7.2) was added. A multiwell plate made out of paper was produced by printing circles in the shape of the wells of a 96-well plate onto Whatman No. 1 chromatography paper (GE Healthcare, Little Chalfont, United Kingdom) using a wax printer essentially as previously described (Pollock et al. Sci Transl Med. 2012; 4(152):152ra129). 5 µL from each solution was then spotted onto the wells on the paper. A picture of the plate was taken using a Canon PowerShot SX150 IS digital camera (Canon Inc., Tokyo, Japan) through a hole in a cardboard box to prevent light from the environment to disturb the measurement (see FIG. 1A). The picture was then analyzed by extracting the red and blue color channels and calculating the average intensity of the pixels.

Figure 6B:
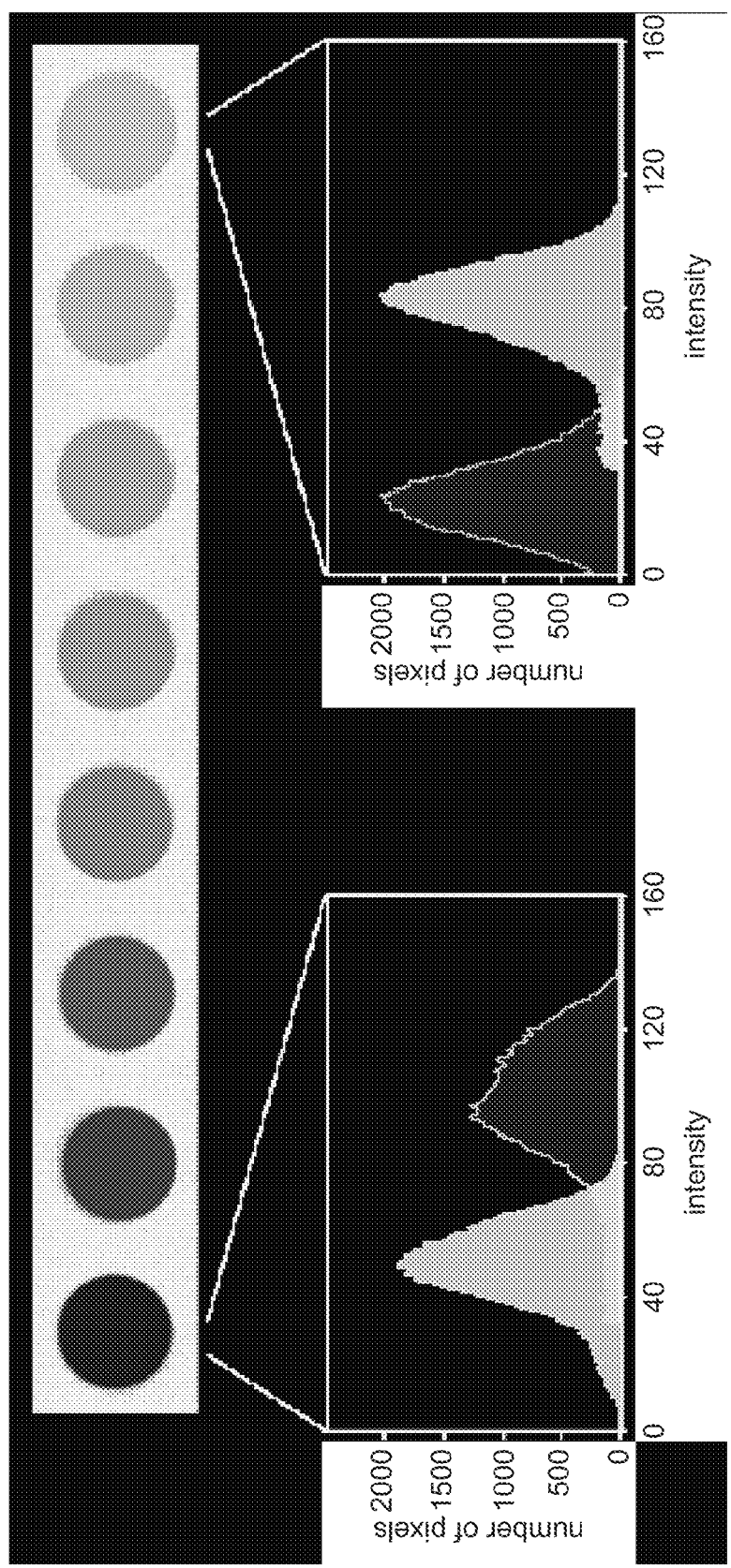
Figure 6C:
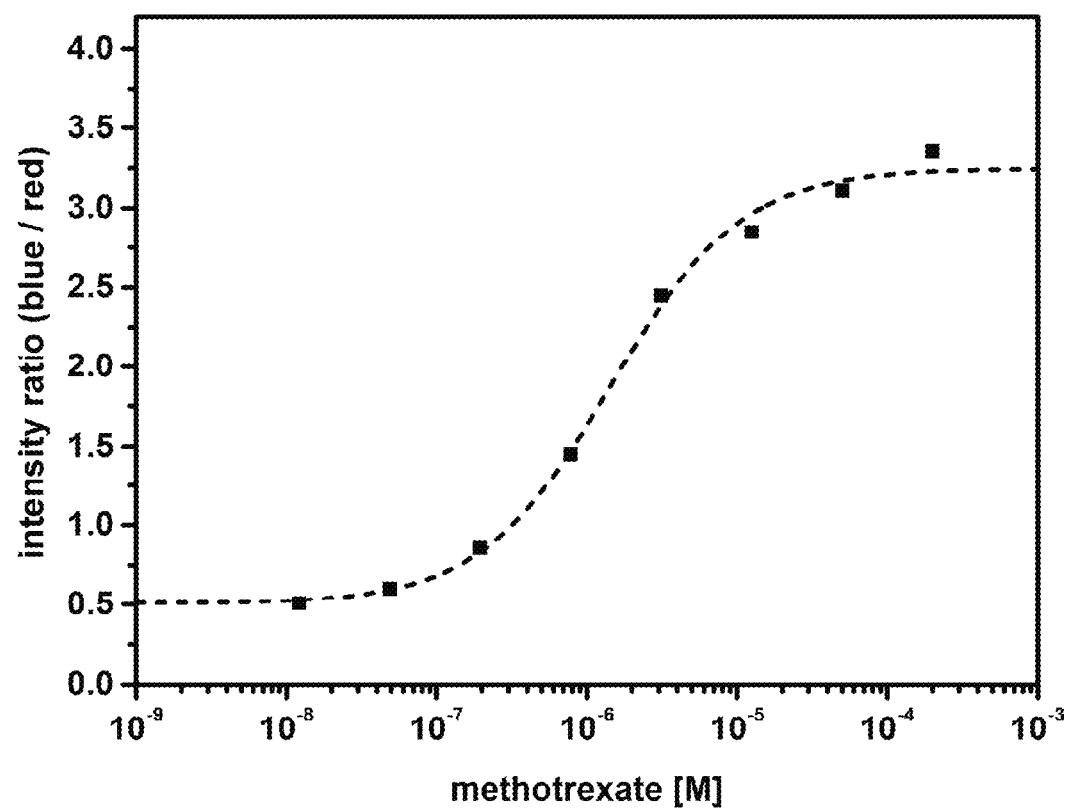

FIG. 6B shows the resulting picture and the histograms that show the intensity distributions of the pixels in the red and blue channels of two wells. FIG. 6C shows the ratio between the average pixel intensity of the blue channel divided by the average pixel intensity of the red channel at different methotrexate concentrations. A similar result as with measurements using a plate reader is observed (see Example 2).

Example 7

Physically Immobilized BRET-Sensor

This example describes the synthesis and physical immobilization of a BRET sensor capable of sensing concentrations of the drug topiramate (Topamax; described in Example 1) on a glass slide to provide an analytical device. The sensor comprises human carbonic anhydrase II (HCA) as a binding protein, an aromatic sulfonamide as an intramolecular ligand. Luciferase and TMR form the BRET pair (see FIG. 1A,B). In addition, at the N-terminus of the sensor molecule the AviTag peptide sequence for the biotinylation of the sensor is added (Beckett, Dorothy; Kovaleva, Elena; Schatz, Peter J. (2008) Protein Science 8 (4): 921-9). A synthetic regulatory molecule containing an O6-benzylguanine (BG) group for SNAP-tag labeling, the fluorophore tetramethylrhodamine (TMR), and 4-(aminomethyl)benzenesulfonamide (aminomethylSA) as tethered ligand was synthesized according to Scheme 1 of Example 1.

The fusion protein is expressed in the *E. coli* strain Rosetta-gami and purified using a C-terminal His-tag. The sensor molecule is assembled by labeling SNAP-tag with the synthetic molecule BG-TMR-aminomethylSA (FIG. 1B of Example 1). The protein is labelled with biotin by incubation with biotin ligase BirA, biotin and ATP. Biotinylated sensor molecule is diluted to a final concentration of 1 µg/µl. The protein solution is added as a thin film to a commercially available glass slide covered with streptavidin (Arrayit Corporation). The glass slide is incubated for 30 min at 4° C. at ambient humidity to allow binding of the biotinylated sensor molecule to immobilized streptavidin. The glass slide is subsequently washed and blocked with commercially available Mocking buffer (Arrayit Corporation). The glass slide is then washed three times with PBS and once with 0.1× PBS, spin dried using a Microarray centrifuge and stored at 4° C. To evaluate the response of the immobilized BRET sensor to different topiramate concentrations, solutions containing defined concentrations of topiramate and coelenterazine-h (NanoLight, Pinetop, Ariz.) in HEPES buffer are spotted onto the glass slide and the signal is collected using a camera as described in Example 6.

The invention claimed is:

1. A sensor molecule for detecting an analyte of interest in a sample using bioluminescence resonance energy transfer (BRET), the BRET sensor molecule comprising a proteinaceous moiety tethered to a synthetic regulatory molecule, wherein
   (i) the proteinaceous moiety comprises a luciferase enzyme attached to a binding protein (BP) capable of binding the analyte of interest;
   (ii) the synthetic regulatory molecule comprises a ligand (L) capable of intramolecular binding to the BP, and a fluorescent acceptor that can accept the energy from the Luc through resonance energy transfer in the presence of the appropriate luciferase enzyme substrate, and
   (iii) wherein the binding of analyte to BP changes the degree of intramolecular binding of L to the BP of the BRET sensor molecule, thereby resulting in a change in BRET efficiency.

2. Sensor molecule according to claim 1, wherein the synthetic regulatory molecule is site-specifically tethered to the proteinaceous moiety.

3. Sensor molecule according to claim 2, wherein the synthetic regulatory molecule is site-specifically tethered to the proteinaceous moiety via a self-labelling protein and wherein the synthetic regulatory molecule is tethered via the appropriate reactive group.

4. Sensor molecule according to claim 1 wherein the luciferase enzyme is nanoluciferase (NanoLuc).

5. Sensor molecule according to claim 1, wherein said analyte of interest is a drug, a metabolite, a protein, a biomarker or a nucleic acid molecule.

6. Sensor molecule according to claim 5,
   wherein said BP is dihydrofolate reductase (DHFR) or a circularly permuted variant thereof, optionally in combination with trimethoprim, methotrexate, or variant thereof as intramolecular ligand;
   wherein said BP is human carbonic anhydrase (HCA), optionally in combination with 4-(aminomethyl) benzenesulfonamide or variant thereof as intramolecular ligand;
   wherein said BP is FK506 binding protein (FKBP), optionally in combination with trimethoxyphenyl prolinamide benzanilide or variant thereof as intramolecular ligand;
   wherein said BP is DIG10.3, optionally in combination with progesterone or variant thereof as intramolecular ligand; or
   wherein said BP is cyclophilin A (CypA) or a circularly permuted variant thereof, optionally in combination with ethyl 5-(p-aminobenzyl)-hydantoate, cyclosporine A, or variant thereof, as intramolecular ligand.

7. An analytical device comprising a BRET sensor molecule according to claim 1, wherein the sensor molecule is arranged in such a manner that, when the device is in use for detecting an analyte of interest in a sample, the photons that are emitted from the sensor molecule and that are collected by a detector pass through the sample for a distance shorter than 330 µm.

8. Device according to claim 7, wherein the sensor molecule is immobilized or absorbed to a solid carrier; is absorbed to a paper carrier or a gel; or confined in a tube, capillary or (microfluidic) chamber.

9. Device according to claim 8, wherein the sensor molecule is absorbed to a chromatography paper or filter paper.

10. Kit of parts, comprising a BRET sensor molecule according to claim 1 and a solid carrier.

11. Kit according to claim 10, further comprising a luciferase substrate.

12. Kit according to claim 10, wherein the sensor molecule is immobilized or absorbed to a solid carrier; is absorbed to a paper carrier or a gel; or confined in a tube, capillary or (microfluidic) chamber.

13. Kit according to claim 12, wherein the sensor molecule is absorbed to a chromatography paper or filter paper.

14. A method for the in vitro detection of an analyte of interest in a sample using bioluminescence resonance energy transfer (BRET), comprising the steps of:
   a) contacting the sample with a BRET sensor according to claim 1;
   b) analyzing energy resonance transfer under conditions wherein the BRET sensor is immobilized or absorbed to a solid carrier.

15. Method according to claim 14, wherein the sample is a biological sample or a fraction thereof.

16. Method according to claim 14, wherein the sample absorbs light in the blue light region.

17. A method for in vitro detecting an analyte of interest in a sample using bioluminescence resonance energy transfer (BRET), comprising the steps of:
   (a) contacting the sample with a BRET sensor molecule according to claim 1 under conditions allowing for an analyte-induced BRET change to occur; and
   (b) analyzing energy resonance transfer.

18. Method according to claim 17, wherein step (b) is performed in solution.

19. Method according to claim 17, comprising the use of an analytical device comprising a BRET sensor molecule for detecting an analyte of interest in a sample using bioluminescence resonance energy transfer (BRET), the BRET sensor molecule comprising a proteinaceous moiety tethered to a synthetic regulatory molecule, wherein
   (i) the proteinaceous moiety comprises a luciferase enzyme attached to a binding protein (BP) capable of binding the analyte of interest;
   (ii) the synthetic regulatory molecule comprises a ligand (L) capable of intramolecular binding to the BP, and a fluorescent acceptor that can accept the energy from the luciferase enzyme through resonance energy transfer in the presence of the appropriate luciferase substrate, and
   wherein the binding of analyte to BP changes the degree of intramolecular binding of L to the BP of the BRET sensor molecule, thereby resulting in a change in BRET efficiency,
   wherein the sensor molecule is arranged in such a manner that, when the device is in use for detecting an analyte of interest in a sample, the photons that are emitted from the sensor molecule and that are collected by a detector pass through the sample for a distance shorter than 330 μm.

* * * * *